US012018332B2

(12) United States Patent
Goggins et al.

(10) Patent No.: US 12,018,332 B2
(45) Date of Patent: Jun. 25, 2024

(54) TELOMERE FUSIONS AND THEIR DETECTION OF DYSPLASIA AND/OR CANCER

(71) Applicant: THE JOHNS HOPKINS UNIVERSITY, Baltimore, MD (US)

(72) Inventors: Michael Goggins, Baltimore, MD (US); Tatsuo Hata, Sendai (JP)

(73) Assignee: The Johns Hopkins University, Baltimore, MD (US)

( * ) Notice: Subject to any disclaimer, the term of this patent is extended or adjusted under 35 U.S.C. 154(b) by 484 days.

(21) Appl. No.: 16/648,847

(22) PCT Filed: Sep. 24, 2018

(86) PCT No.: PCT/US2018/052342
§ 371 (c)(1),
(2) Date: Mar. 19, 2020

(87) PCT Pub. No.: WO2019/060801
PCT Pub. Date: Mar. 28, 2019

(65) Prior Publication Data
US 2020/0255903 A1  Aug. 13, 2020

Related U.S. Application Data

(60) Provisional application No. 62/561,785, filed on Sep. 22, 2017.

(51) Int. Cl.
C12P 19/34 (2006.01)
C12Q 1/686 (2018.01)
C12Q 1/6886 (2018.01)

(52) U.S. Cl.
CPC ........... C12Q 1/6886 (2013.01); C12Q 1/686 (2013.01); *C12Q 2600/118* (2013.01); *C12Q 2600/156* (2013.01)

(58) Field of Classification Search
CPC .............................. C12Q 1/686; C12Q 1/6886
See application file for complete search history.

(56) References Cited

U.S. PATENT DOCUMENTS

| | | |
|---|---|---|
| 5,837,453 A | 11/1998 | Harley et al. |
| 8,632,983 B2 | 1/2014 | Haab et al. |
| 9,341,628 B2 | 5/2016 | Finkelstein et al. |
| 2014/0024034 A1 | 1/2014 | Tanaka |
| 2014/0100124 A1 | 4/2014 | Wylie et al. |
| 2014/0155465 A1* | 6/2014 | Bassett ............... C12Q 1/6886 435/6.12 |
| 2016/0186250 A1 | 6/2016 | Harley et al. |
| 2017/0137893 A1* | 5/2017 | Baird ................ C12Q 1/6886 |

FOREIGN PATENT DOCUMENTS

| | | |
|---|---|---|
| WO | 2009092108 A2 | 7/2009 |
| WO | 2011031560 A2 | 3/2011 |
| WO | 2013074438 A1 | 5/2013 |

OTHER PUBLICATIONS

Duell, Gut 66(6), 986-987 (Jun. 2017). (Year: 2017).*
Rychlik et al., Nucleic Acids Research 17(21), 8543-8551 (1989). (Year: 1989).*
Wahl et al., Molecular Hybridization of Immobilized Nucleic Acids: Theoretical Concepts and Practical Considerations., (1987) Methods Enzymol. 152:399.
Kimmel., Identification and Characterization of Specific Clones: Strategy for Confirming the Validity of Presumptive Clones (1987) Methods Enzymol. 152:507.
Benton et al., Screening lambdagt recombinant clones by hybridization to single plaques in situ., Science 196:180, 1977.
Grunstein et al., Colony hybridization: a method for the isolation of cloned DNAs that contain a specific gene., Proc. Natl. Acad. Sci., USA 72:3961, 1975.
De Lange., How telomeres solve the end-protection problem. Science 2009;326:948-52.
O'Sullivan et al., Telomeres: protecting chromosomes against genome instability. Nat Rev Mol Cell Biol 2010;11:171-81.
Maser et al., Connecting chromosomes, crisis, and cancer. Science 2002;297:565-9.
Tanaka et al., The presence of telomere fusion in sporadic colon cancer independently of disease stage, TP53/KRAS mutation status, mean telomere length, and telomerase activity. Neoplasia 2014;16:814-23.
Meeker et al., Telomere shortening occurs in subsets of normal breast epithelium as well as in situ and invasive carcinoma. Am J Pathol 2004;164:925-35.
Meeker et al. Telomere length abnormalities occur early in the initiation of epithelial carcinogenesis. Clin Cancer Res 2004;10:3317-26.
Van Heek et al. Telomere shortening is nearly universal in pancreatic intraepithelial neoplasia. Am J Pathol 2002;161:1541-7.
Hashimoto et al. Telomere shortening and telomerase expression during multistage carcinogenesis of intraductal papillary mucinous neoplasms of the pancreas. J Gastrointest Surg 2008;12:17-28; discussion 28-9.
Heaphy et al. Prevalence of the alternative lengthening of telomeres telomere maintenance mechanism in human cancer subtypes. Am J Pathol 2011;179:1608-15.
Lin et al. Telomere dysfunction and fusion during the progression of chronic lymphocytic leukemia: evidence for a telomere crisis. Blood 2010;116:1899-907.
Tanaka et al. Telomere fusions in early human breast carcinoma. Proc Natl Acad Sci U S A 2012;109:14098-103.

(Continued)

*Primary Examiner* — Kenneth R Horlick
(74) *Attorney, Agent, or Firm* — Johns Hopkins Technology Ventures

(57) ABSTRACT

Described are telomere fusion assays to detect dysplasia in subjects using nested primers. The methods of the present invention are able to detect dysplasia in subjects with intraductal papillary mucinous neoplasma (IPMNs), for example.

3 Claims, 15 Drawing Sheets

Specification includes a Sequence Listing.

(56) References Cited

OTHER PUBLICATIONS

Lee et al. Telomere extension by telomerase and ALT generates variant repeats by mechanistically distinct processes. Nucleic Acids Res 2014;42:1733-46.

Schmidt et al. Intraductal papillary mucinous neoplasms: predictors of malignant and invasive pathology. Ann Surg 2007;246:644-51; discussion 651-4.

Hong et al. Telomeres are shortened in acinar-to-ductal metaplasia lesions associated with pancreatic intraepithelial neoplasia but not in isolated acinar-to-ductal metaplasias. Mod Pathol 2011;24:256-66.

Wasif et al. Invasive intraductal papillary mucinous neoplasm versus sporadic pancreatic adenocarcinoma: a stage-matched comparison of outcomes. Cancer 2010;116:3369-77.

Poultsides et al. Histopathologic basis for the favorable survival after resection of intraductal papillary mucinous neoplasm-associated invasive adenocarcinoma of the pancreas. Ann Surg 2010;251:470-6.

Yopp et al. Invasive carcinoma arising in intraductal papillary mucinous neoplasms of the pancreas: a matched control study with conventional pancreatic ductal adenocarcinoma. Ann Surg 2011;253:968-74.

Tanaka et al. International consensus guidelines 2012 for the management of IPMN and MCN of the pancreas. Pancreatology 2012;12:183-97.

Canto et al. International Consensus Recommendations on the Management of Patients with Increased Risk for Familial Pancreatic Cancer (The Cancer of the Pancreas Screening (CAPS) Consortium Summit). Gut 2013;62:339-47.

Vasen et al. Benefit of Surveillance for Pancreatic Cancer in High-Risk Individuals: Outcome of Long-Term Prospective Follow-Up Studies From Three European Expert Centers. J Clin Oncol 2016;34:2010-9.

Crippa et al. Low progression of intraductal papillary mucinous neoplasms with worrisome features and high-risk stigmata undergoing non-operative management: a mid-term follow-up analysis. Gut 2016:epub Jan. 9, 2016.

Sahora et al. Branch duct intraductal papillary mucinous neoplasms: does cyst size change the tip of the scale? A critical analysis of the revised international consensus guidelines in a large single-institutional series. Ann Surg 2013;258:466-75.

Hruban et al. An illustrated consensus on the classification of pancreatic intraepithelial neoplasia and intraductal papillary mucinous neoplasms. Am J Surg Pathol 2004;28:977-87.

Stohr et al., The terminal telomeric DNA sequence determines the mechanism of dysfunctional telomere fusion. Mol Cell 2010;39:307-14.

Ijdo et al. Origin of human chromosome 2: an ancestral telomere-telomere fusion. Proc Natl Acad Sci U S A 1991;88:9051-5.

Hata et al. Cyst fluid telomerase activity predicts the histologic grade of cystic neoplasms of the pancreas. Clin Cancer Res 2016.

Maker et al. Cyst fluid interleukin-1beta (IL 1beta) levels predict the risk of carcinoma in intraductal papillary mucinous neoplasms of the pancreas. Clin Cancer Res 2011;17:1502-8.

Matthaei et al. miRNA biomarkers in cyst fluid augment the diagnosis and management of pancreatic cysts. Clin Cancer Res 2012;18:4713-24.

Schmidt et al. PGE(2) in pancreatic cyst fluid helps differentiate IPMN from MCN and predict IPMN dysplasia. J Gastrointest Surg 2008;12:243-9.

Brugge et al. Diagnosis of pancreatic cystic neoplasms: a report of the cooperative pancreatic cyst study. Gastroenterology 2004;126:1330-6.

Jones et al. Core signaling pathways in human pancreatic cancers revealed by global genomic analyses. Science 2008;321:1801-6.

Griffin et al. Molecular cytogenetic characterization of pancreas cancer cell lines reveals high complexity chromosomal alterations. Cytogenet Genome Res 2007;118:148-56.

Cui et al. Genetically defined subsets of human pancreatic cancer show unique in vitro chemosensitivity. Clin Cancer Res 2012;18:6519-30.

Lee et al. Notch 2-positive progenitors with the intrinsic ability to give rise to pancreatic ductal cells. Lab Invest 2005;85:1003-12.

Capper et al. The nature of telomere fusion and a definition of the critical telomere length in human cells. Genes Dev 2007;21:2495-508.

Letsolo et al., Fusion of short telomeres in human cells is characterized by extensive deletion and microhomology, and can result in complex rearrangements. Nucleic Acids Res 2010;38:1841-52.

Brown et al. Structure and polymorphism of human telomere-associated DNA. Cell 1990;63:119-32.

Cawthon., Telomere length measurement by a novel monochrome multiplex quantitative PCR method. Nucleic Acids Res 2009;37:e21.

Marciniak, R., et al., "A Novel Telomere Structure in a Human Alternative Lengthening of Telomeres Cell Line" Cancer Res 2005; 65(7): 2730-7).

Helias-Rodzewicz, Z., et al., "Subtelomeric rearrangements detected by Fish in three of 33 families with idiopathic mental retardation and minor physical anomalies" J Med Genet 2002;39:e53.

Oh, B, et al., "Frequent changes in subtelomeric DNA methylation patterns and its relevance to telomere regulation during human hepatocarcinogenesis" Int. J. Cancer: 128, 857-868 (2011).

Poojary, S., et al., "Dysfunction of subtelomeric methylation and telomere length in gallstone disease and gallbladder cancer patients of North Central India" J Hepatobiliary Pancreat Sci (2016) 23:276-282.

Amato et al. Targeted next-generation sequencing of cancer genes dissects the molecular profiles of intraductal papillary neoplasms of the pancreas. J Pathol 2014;233:217-27.

Tan et al. GNAS and KRAS Mutations Define Separate Progression Pathways in Intraductal Papillary Mucinous Neoplasm-Associated Carcinoma. J Am Coll Surg 2015;220:845-54 e1.

Gisselsson et al. Telomere dysfunction triggers extensive DNA fragmentation and evolution of complex chromosome abnormalities in human malignant tumors. Proc Natl Acad Sci U S A 2001;98:12683-8.

Ridtitid et al., Management of branch-duct intraductal papillary mucinous neoplasms: a large single-center study to assess predictors of malignancy and long-term outcomes., Gastrointestinal Enterology 2016, 84(3):436.

Mukewar et al., Fukuoka criteria accurately predict risk for adverse outcomes during follow-up of pancreatic cysts presumed to be intraductal papillary mucinous neoplasms., Gut 2017, 66:1811-1817.

Yamada et al., Comparison of the international consensus guidelines for predicting malignancy in intraductal papillary mucinous neoplasms., 2016 Surgery, 159(3):878-884.

Laeseke et al., Combining in Vitro Diagnostics with in Vivo Imaging for Earlier Detection of Pancreatic Ductal Adenocarcinoma: Challenges and Solutions, 2015 Radiology 277:644.

Majumdar et al., Molecular detection of pancreatic neoplasia: Current status and future promise., World J Gastroenterol 2015, 21(40):11387.

* cited by examiner

Figure 2
A
| | Cancer Cell lines | IPMN IGD | IPMN HGD |
|---|---|---|---|
| Telomere – subtelomere fusion 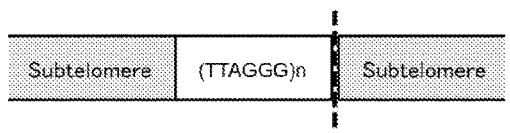 | 20/31 | 3/49 | 12/25 |
| Telomere – telomere fusion 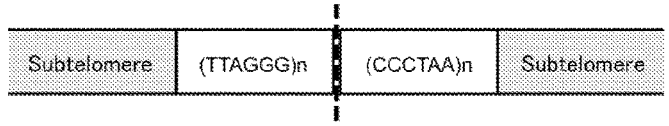 | 1/31 | 0/49 | 0/25 |
| Telomere – complex fusion 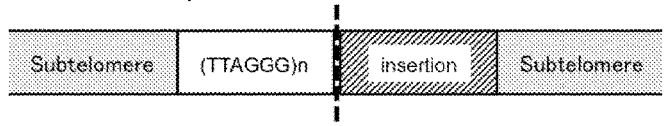 | 3/31 | 0/49 | 0/25 |
B
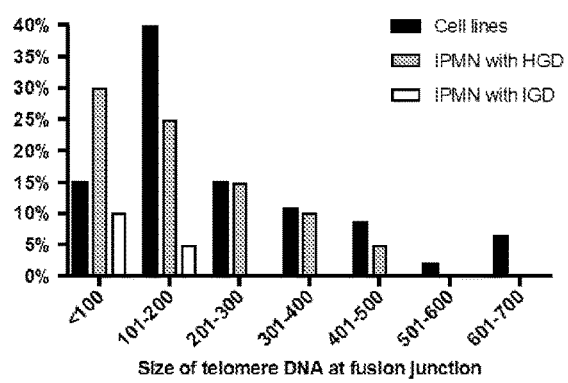
Size of telomere DNA at fusion junction
C
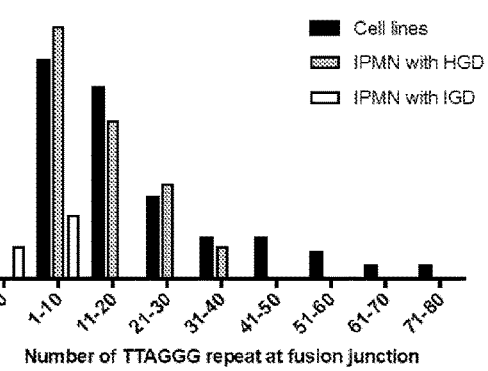
Number of TTAGGG repeat at fusion junction

Figure 6 q-subtel 2 primer

|CACCGAGATTCTCCCAAGGCAAG|GCGAGGGGCTGTATTGCAGGGTTCAACTGCAGCGTCG

CAACTCAAATGCAGCATTCCTAATGCACACATGACACCCAAAATATAACAGACATATTAC

TCATGGAGGGTTAGGGTTGGGGTTGGGGTTGGGGTTGGGGTTAGGGTTAGGGTTAGGGTT

AGGGGTTAGGGTTAGGGGTTAGGGTTAGGGTTAGGGTTAAGGGTTAGGGTTAAGGGTTAGGGTTAG

GGTTAGGGTTAGGGTTAGGGTTAGGGTTAGGGTTTAGCGGTTAGGGTTGGGGTTGGCGT

TGGGGTAGGGGTTGGGGTTGGGGTAGGGGTAGGGGTTGGGGTTGGGGTAGGGGTAGGGGT

AGGGTTAGGGTTAGGGTTAGGGTTAGGGGTTAGGGTTAGGATAGACATGAAGATGGGGT 1p, 22q telomere ←⊔→ 9q21

CACCTCCCATCCACCAGCAACCTCCCTGTACACTGCCGCAGGTGCAGCAGCAGTTCTTTG

CACTGGGAGCCAATGAGAGTGTGCACTGGGGGAAAGCATTTTTCACACTTTTCATGTCTG

TTGCCCTCTACCCCCAAGTAAACCCTGACTTCTGGGGCTTTCACAGTGGTAAAGTGAGC

9q21 ←⊔→ 11q23

ACAATTACAGAATCTACCTAATAGGGCTGTCTGTATGTCAATGGACTTGGCCTGTGCCTG

AGGAAATGCTAGCCCCATGATCCTGCAGCCATGGTTAGGAAGGACACGGCAGGGAATGGG

ACCTTTCACAGACCGGGCCGTGGCCAGCAGCCAGGGCCGACTCACCGAGAACAATGGCGA

GCATCTGAGTGGCTTTCCTTTGGTCATAGGCGTGGCGCAGGCGCAGAGAGGCGCGCCGTG

11q23 ←⌐           → 1p, 9p, 15p subtelomere

CTGCCG|CAGGCGCAGAGACACATGCTAG| p-subtel 2 primer

Figure 7
A
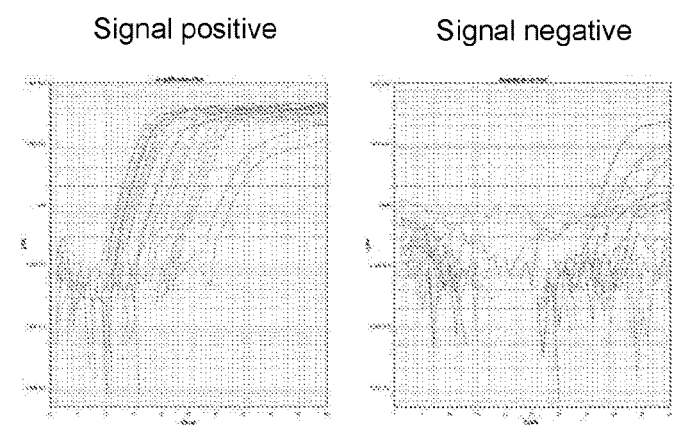
B
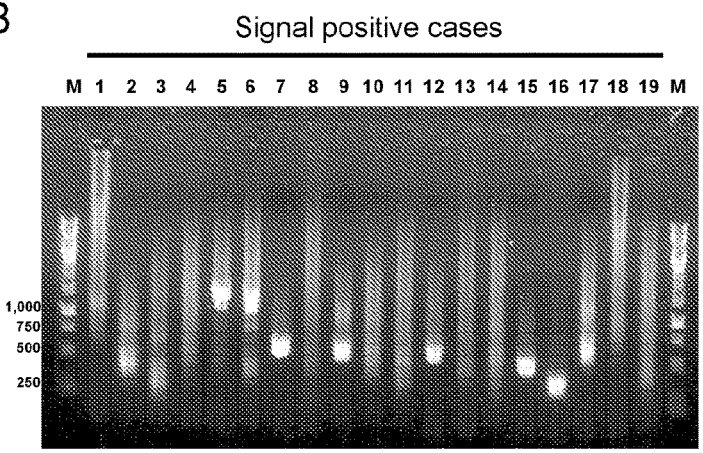
C
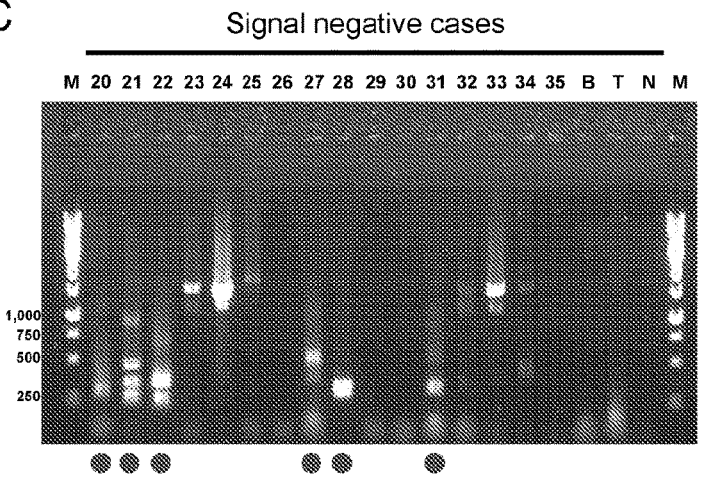
D
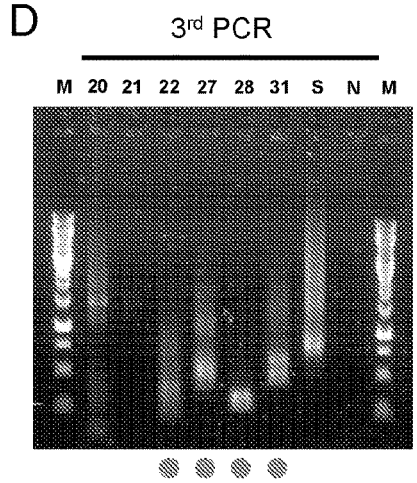

Figure 13
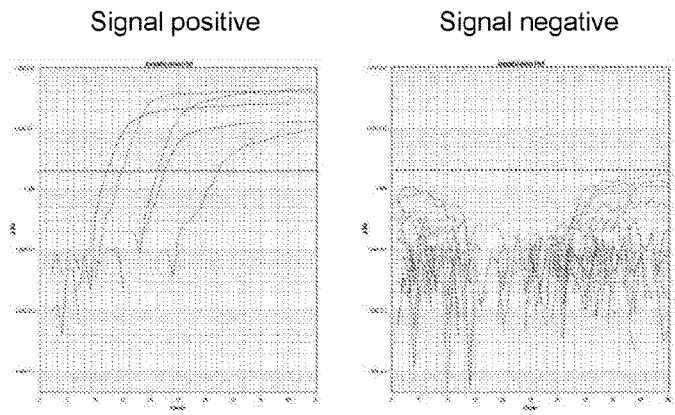
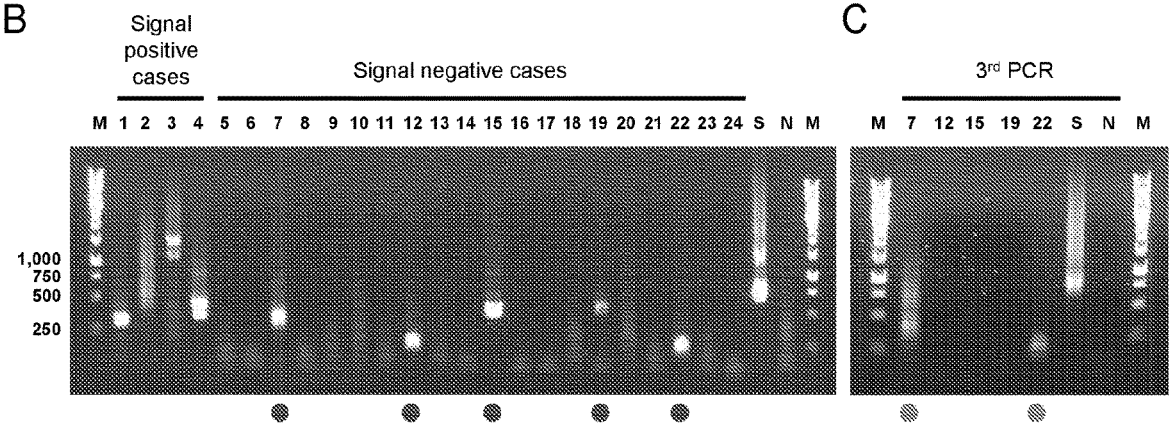

Figure 14
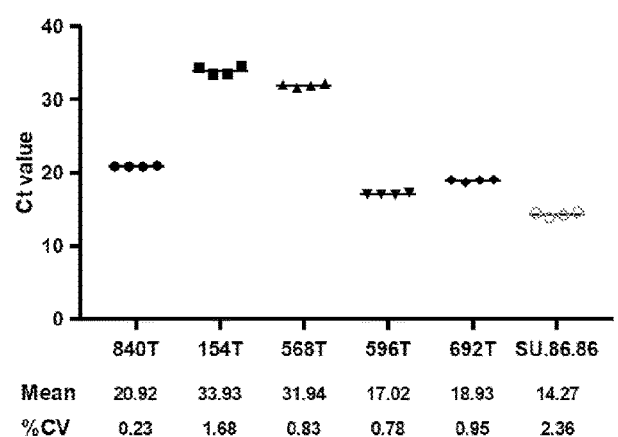
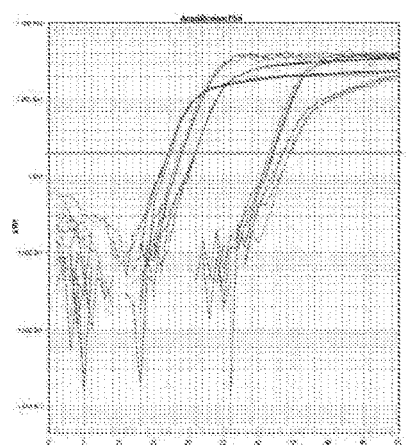
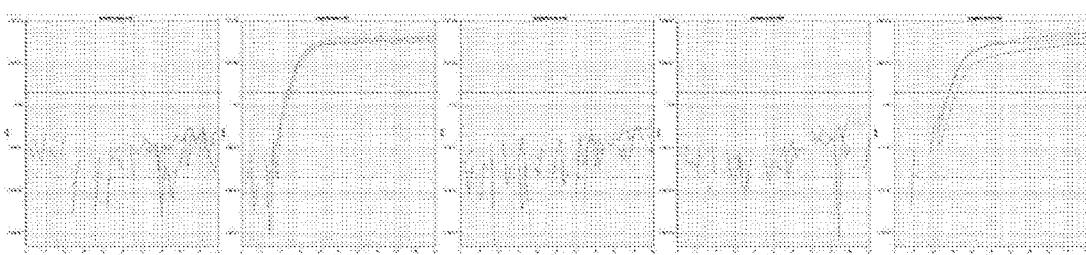

Figure 15
A
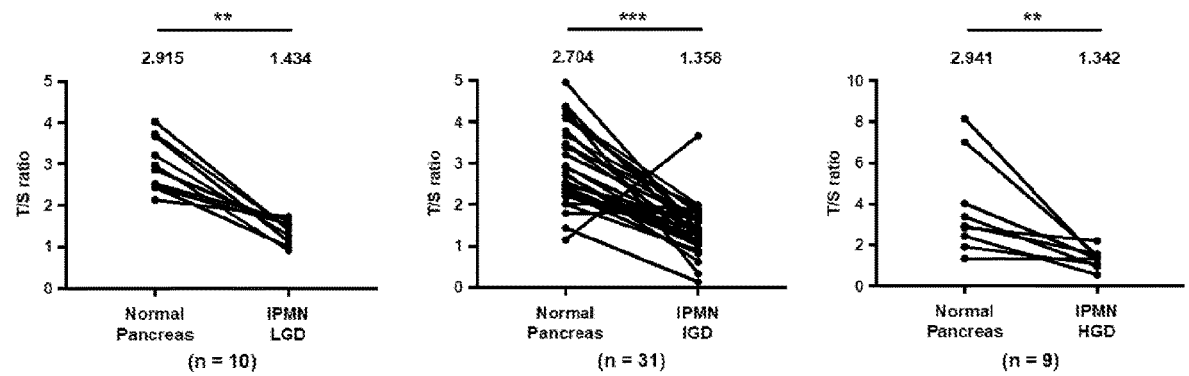
B
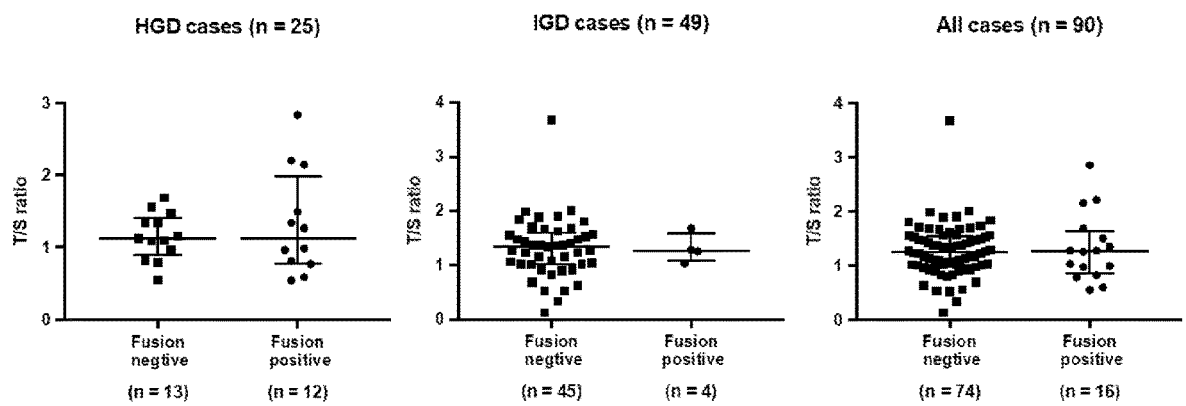
C
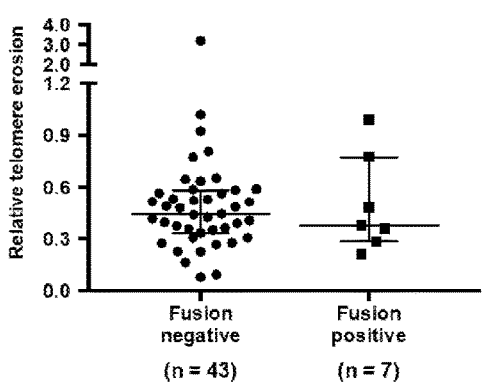
D
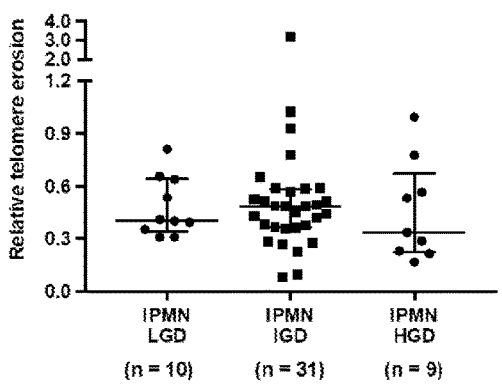

TELOMERE FUSIONS AND THEIR DETECTION OF DYSPLASIA AND/OR CANCER

CROSS-REFERENCE TO RELATED APPLICATIONS

This application is a 35 U.S.C. § 371 U.S. national entry of International Application PCT/US2018/052342, having an international filing date of Sep. 24, 2018, which claims the benefit of U.S. Provisional Application No. 62/561,785, filed Sep. 22, 2017, the content of each of the aforementioned applications is herein incorporated by reference in their entireties.

STATEMENT OF GOVERNMENTAL INTEREST

This invention was made with government support under grant nos. CA062924, CA176828, CA210170 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 21, 2018, is named P14622-02_SL.txt and is 30,797 bytes in size.

BACKGROUND OF THE INVENTION

Telomeres are structures present at all chromosomal ends, comprising hexameric

DNA repeat sequences (TTAGGG). Telomeric repeat sequences prevent fusion between chromosomal ends; such end-to-end fusions can occur once telomeres lose most or all of their telomere repeat sequences. Telomere fusions that arise in critically short telomeres will either elicit DNA damage responses leading to cell death or cause breakage-fusion-breakage cycles with ongoing chromosomal instability, which is a major mechanism that contributes to the progression of many precancerous neoplasms to invasive cancers. Most cancer cells display significant telomere shortening and telomere shortening is observed in most pancreatic intraepithelial neoplasia (PanIN) lesions including PanIN-1A. Similarly, Intraductal papillary mucinous neoplasms (IPMNs) with low-grade dysplasia (LGD) typically have significant telomere shortening. Neoplastic cells with critically shortened telomeres can maintain their shortened telomere length and overcome cell death by activating telomerase (the most common mechanism), or occasionally by using the alternate length telomere (ALT) pathway.

Telomere fusions that arise from critical telomere shortening have been observed not only in cancers, but were also identified in 13% of colorectal adenomas in one study, and thus could be expected to occur in other precursor lesions that have critically shortened telomeres. If so, the detection of telomere fusions in diagnostic specimens could help identify precancerous neoplasms with critically short telomeres more likely to progress to invasive cancer.

IPMNs, are one such precursor lesion, characterized by the papillary proliferation of mucin-producing epithelial cells and cystic dilatation of the main or branch pancreatic duct, and are the most common type of neoplastic cyst. The main goal of the diagnostic evaluation of IPMNs is to determine their grade of dysplasia, i.e. to distinguish IPMNs with LGD, having low malignant potential and a favorable prognosis and not requiring surgical intervention from those that have high-grade dysplasia (HGD), or an associated invasive carcinoma. Some IPMNs have an intermediate-grade of dysplasia (IGD). Once IPMN progresses to invasive carcinoma, it is associated with a poor prognosis, with average 5-year survival ranging from 22% to 67%. Given the morbidity and risks related to pancreatic surgery, watchful observation is generally appropriate for patients with IPMNs with LGD and IGD, unless patients have other risk factors for progression or extensive multifocal disease.

The management of pancreatic cystic tumors is based on clinical evaluation and pancreatic imaging findings in accordance with international consensus guidelines 2012. Surgical intervention is recommended for cases with "high-risk stigmata"; cases with "worrisome features" should undergo the endoscopic ultrasonography (EUS) analysis for further evaluation and "low-risk" cases can undergo transabdominal imaging. These guidelines are useful but pancreatic imaging does not provide sufficient information about the neoplastic nature of a pancreatic cyst. Better characterization of pancreatic cysts could allow more patients with worrisome cysts to be continue with surveillance. Cyst fluid biomarkers are being evaluated for their utility to better predict the neoplastic nature of IPMNs. Although cyst fluid analysis can yield information about the molecular characteristics of the cyst, additional markers are needed that provide evidence of progression to high-grade dysplasia and invasive cancer.

SUMMARY OF THE INVENTION

One embodiment of the present invention is a method of determining the grade of dysplasia or cancer in a subject comprising the steps of: obtaining a biological sample comprising DNA from a subject; contacting the biological sample with a first primer; conducting a first PCR amplification reaction to form a first PCR product; contacting the first PCR product with a nested PCR primer located internal to the first primer; conducting a second PCR amplification to form a second PCR product; analyzing the second PCR product for amplified nucleic acid sequences indicating the present of telomere fusions in the biological sample; and determining the grade of dysplasia or cancer in the subject by the presence of telomere fusions in the biological sample. The biological sample could be pancreatic tissue, cells, or fluid such as pancreatic cyst fluid taking from a subject thought to have pancreatic cyst intraductal papillary mucinous neoplasm. Suitable first primers and nested primers of the present invention are located on each side of a telomere repeat region and are selected from the group comprising a subtelomere q armPCR (q-subtel) primer, a subtelomere p-arm PCR (p-subtel) primer; or a combination thereof. The nested primers are internal to the first primer by annealing to a nucleic acid regions closer to the telomere repeat region than the first primer. Suitable subtelomere q armPCR (q-subtel) primers anneal to nucleic acids in a subtelomeric region consisting of 1p, 1q, 2q, 4p, 5q, 6q, 9p, 10q, 13q, 16p, 16q, 19p, 21q, 22q, or Xq or a combination thereof. Suitable subtelomere p-arm PCR (P-subtel) primers anneal to nucleic acid sequences in a subtelomeric region consisting of 1p, 9P, 12P, 15q, 16p, Xp, Yq or a combination thereof. Examples of first primers include (p-subtel 1 primer) GACGCGCTAGCATGTGTCTCTG (SEQ ID NO: 1); (q-subtel 1 primer) GAATCCTGCGCACCGAGATTCTC (SEQ ID NO: 2); (XpYp primer) GGCTCAGGCAGTCTGCTTTTATTC (SEQ ID NO: 3); or a combination thereof. Examples of nested primer include (p-subtel 2 primer) CTAGCATGTGTCTCTGCGCCTG (SEQ ID NO: 4); (q-subtel 2 primer) CACCGAGATTCTCCCAAGGCAAG (SEQ ID NO: 5); (XpYp primer) CTCTAATCTGCTCCCACCCACATC (SEQ ID NO: 6); or a combination thereof. PCR amplification methods used in the present invention include most PCR methods including qPCR amplification.

Another embodiment of the present invention is a kit for determining the grade of dysplasia or cancer in a subject comprising, a first primer; and a nested PCR primer located internal to the first primer; wherein the first primer and the nested primer are selected from the group comprising a subtelomere q armPCR (q-subtel) primer, a subtelomere p-arm PCR (p-subtel) primer; or a combination thereof.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "disease" is meant any condition or disorder that damages or interferes with the normal function of a cell, tissue, or organ. Examples of diseases include cancer.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "express" refers to the ability of a gene to express the gene product including for example its corresponding mRNA or protein sequence(s).

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The term, "obtaining" as in "obtaining an agent" includes synthesizing, purchasing, or otherwise acquiring the agent.

The term "qPCR" refers to a real-time polymerase chain reaction (Real-Time PCR), is a laboratory technique of molecular biology based on the polymerase chain reaction (PCR). It monitors the amplification of a targeted DNA molecule during the PCR, i.e. in real-time, and not at its end, as in conventional PCR. Real-time PCR can be used quantitatively (quantitative real-time PCR), and semi-quantitatively, i.e. above/below a certain amount of DNA molecules (semi quantitative real-time PCR). Two common methods for the detection of PCR products in real-time PCR are: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence.

A "reference" refers to a standard or control conditions such as a sample (human cells) or a subject that is a free, or substantially free, of an agent such as one or more inhibitors of IDO1 and/or a vaccine.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence.

As used herein, the term "specificity" is the percentage of subjects correctly identified as having a particular disease i.e., normal or healthy subjects. For example, the specificity is calculated as the number of subjects with a particular disease as compared to non-cancer subjects (e.g., normal healthy subjects).

By "specifically binds" is meant a compound or antibody that recognizes and binds a polypeptide of the invention, but which does not substantially recognize and bind other molecules in a sample, for example, a biological sample, which naturally includes a polypeptide of the invention.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100·mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Such treatment (surgery and/or chemotherapy) will be suitably administered to subjects, particularly humans, suffering from, having, susceptible to, or at risk for pancreatic cancer or disease, disorder, or symptom thereof. Determination of those subjects "at risk" can be made by any objective or subjective determination by a diagnostic test or opinion of a subject or health care provider (e.g., genetic test, enzyme or protein marker, a marker (as defined herein), family history, and the like).

BRIEF DESCRIPTION OF THE DRAWINGS

FIG. 2A-2C characterizes the telomere fusions. (A) Classification of telomere fusions in pancreatic cancer cell lines and IPMN tissues. Telomere-telomere fusions contain telomere repeat sequences from both chromosomal ends (TTAGGG and its complement CCCTAA). Telomere-subtelomere fusions contain telomeric repeats from one chromosome fused with the subtelomeric region of another chromosome. Telomere-complex fusions contain short insertion between the subtelomere-telomere fusion junction. (B) The length of telomeric DNA within fusion junctions. (C) The number of TTAGGG repeats within fusions.

FIG. 6 illustrates the DNA sequence of a telomere fusion from PANC 486 (clone 4) cells (SEQ ID NO: 77). Open rectangles indicate primer sequences and telomeric repeats were underlined.

FIG. 7A-7D illustrates representative results of telomere fusion assays in pancreatic cancer xenograft samples. (A) Amplification curves after nested-qPCR classified by signal positive and negative. (B) Gel-imaging after the electrophoresis of signal positive nested-qPCR products. (C) Gel-imaging after the electrophoresis of signal negative nested-qPCR products. Samples marked with blue color circles are applied to 3rd PCR. (D) Gel-imaging after the electrophoresis of 3rd PCR. Samples marked with red color circled shows similar size of amplicon compared to nested-qPCR were subcloned and sequenced for validation. B, mouse whole blood DNA; T, mouse tail DNA; S, SU.86.86 cells; N, non-template control; M, DNA marker

FIG. 13A-13E illustrates representative examples of telomere fusion assay results. (A) Nested-qPCR amplification from fusion-positive and fusion-negative cases. (B) Gel-electrophoresis images of nested-qPCR products. Samples marked with blue circles represent PCR-positive but qPCR negative telomere fusion amplicons. (C) Gel-electrophoresis images of 3rd round PCR to further evaluate telomere fusion amplicons. (D, E) Examples of telomere fusion sequences from IPMNs including qPCR-positive (lane 3, D (SEQ ID NO: 80) and qPCR-negative (lane 22, E (SEQ ID NO: 81)) fusions. Open rectangles indicate primer sequences and underlined sequences are telomeric repeats. S, SU.86.86 cell line as positive control; N, non-template control; M, DNA marker FIG. 14A-14C illustrates intra- and inter-assay variation of telomere fusion assay. (A) Ct values of four technical replicates measured by nested-qPCR in the same assay using five representative IPMN DNA samples and the SU.86.86 cell line. Horizontal bars indicate mean values. (B) Amplification curves of five DNA samples corresponding to (A). (C) Inter-assay variation using five representative fusion-positive or fusion-negative DNA samples. CV; coefficient of variation.

FIG. 15A-15D illustrates telomere lengths of IPMN stratified by histologic grade and telomere fusion status. (A) Telomere length measurement and comparison using paired of normal pancreas and IPMN. Median T/S ratio was shown above the aligned dots. (B) Mean Telomere lengths of fusion positive and negative IPMNs. The longer horizontal bar represents the median value and shorter ones represents values of the 75th and 25th percentiles, respectively. (C) Relative telomere erosion between fusion positive and negative IPMN tissues. (D) Relative telomere erosion across the three histologic grades of IPMN. P<0.01, *P<0.001

DETAILED DESCRIPTION OF THE INVENTION

Telomere fusion detection in pancreatic cancer samples

Figure 5:
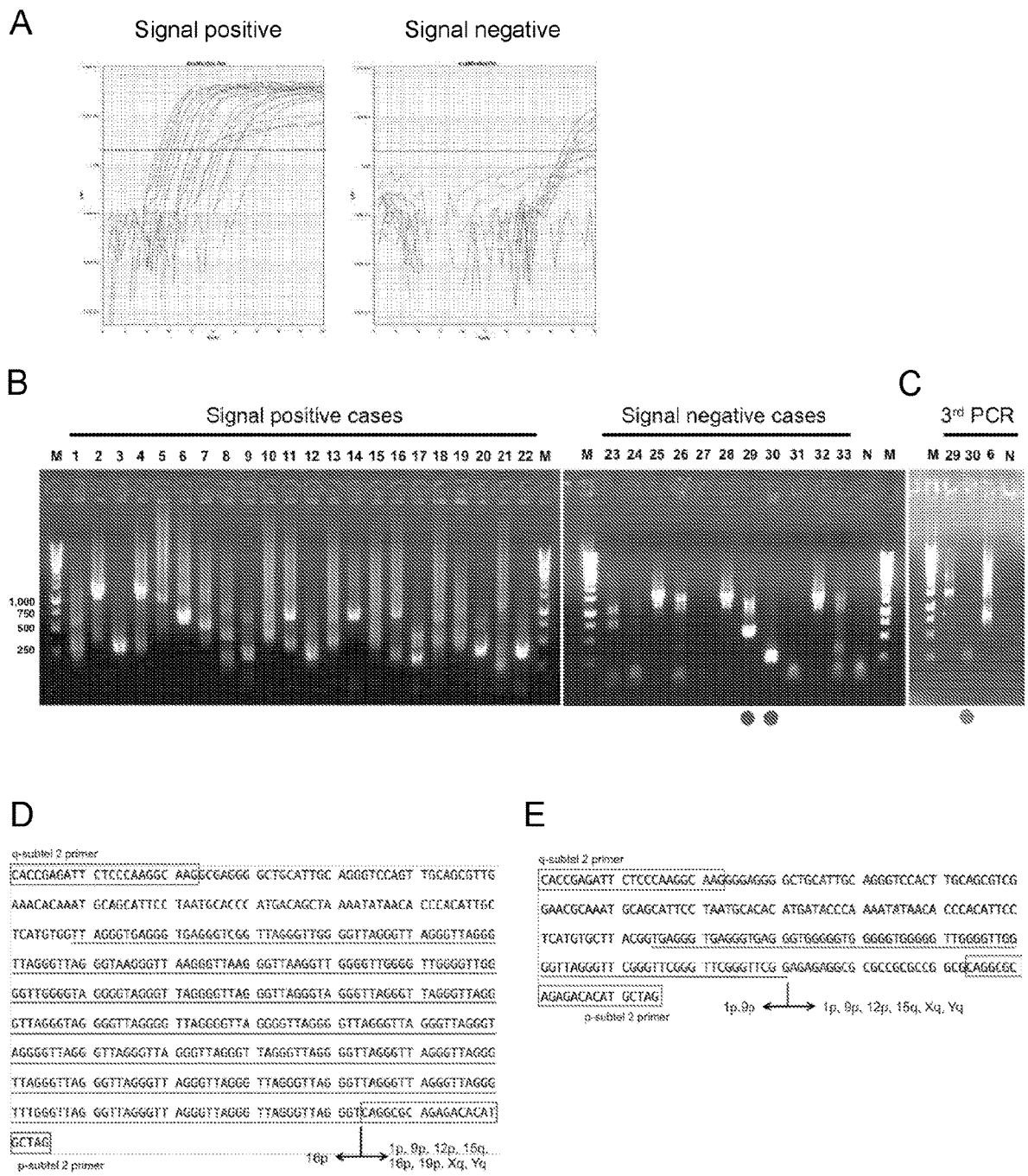
FIG. 5A-5E illustrates examples of telomere fusion assay results. (A) Amplification curves after nested-qPCR classified by signal positive and negative. (B) Gel-imaging after the electrophoresis of nested-qPCR products. Samples marked with blue color circles are applied to 3rd PCR. (C) Gel-imaging after the electrophoresis of 3rd PCR. Sample in lane 30 (PL4 cell line) marked with red color circled shows similar size of amplicon compared to nested-qPCR. (D, E) DNA sequence in one of the subcloned AsPC-1 (SEQ ID NO: 75) (D) and PL4 (SEQ ID NO: 76) (E) fusion junctions. Open rectangles indicate primer sequences and telomeric repeats were underlined. N, non-template control; M, DNA marker

Telomere fusions were detected in 22 of 31 pancreatic cancer cell lines using the telomere fusion assay (FIGS. 5A and 5B). Twenty-one of these fusions were detected using the telomere repeat probe by qPCR. One cell line (PL4) had a telomere fusion with variant telomere repeat sequence, identified first by electrophoresis of the nested-qPCR products and confirmed by an additional nested PCR (lane 30) (marked as red circle, FIG. 5C). A telomere fusion was also detected in HPDE which is known to harbor chromosomal abnormalities, but not in the HPNE line or in normal tissue samples. The presence of telomere fusions in the cancer cell lines was confirmed in all qPCR positive samples by subcloning and sequencing the nested-qPCR products (Table 1).

TABLE 1

Telomere fusion junction sequence analysis of pancreatic cancer cell lines and HPDE.

| Cell line | Clone ID | Fusion chromosomes A | Fusion chromosomes B | Telomeric repeat length (nt) | (TTAGGG)n | SEQ ID NO: | Fusion pattern (fusion chromosome A-B) |
|---|---|---|---|---|---|---|---|
| A32-1 | 3 | 4q, 5q | 1p, 9p, 15q | 173 | 20 | 9 | telomere-subtelomere |
| A32-1 | 4 | 13q | 1p, 9p, 15q | 382 | 31 | 10 | telomere-subtelomere |
| A38-5 | 2 | 8p* | 1p, 9p, 12p, 15q, Xq, Yq | 111 | 10 | 11 | telomere-subtelomere |
| AsPC-1 | 2 | 2q | 1p, 9p, 15q | 359 | 27 | 12 | telomere-subtelomere |
| AsPC-1 | 12 | 16p | 1p, 9p, 12p, 15q, 16p, Xq, Yq | 395 | 46 | 13 | telomere-subtelomere |
| Capan-1 | 6 | 4q, 5q | 1p, 9p, 15q | 76 | 1 | | telomere-subtelomere |
| Capan-1 | 12 | 4q, 5q | 1p, 9p, 15q | 65 | 3 | 14 | telomere-subtelomere |
| Capan-1 | 4 | 4q, 5q | 1p, 9p, 12p, 15q, Xq, Yq | 682 | 51 | 15 | telomere-subtelomere |
| Capan-2 | 6 | Xq, Yq, 1p, 4p, 9p, 16p | 1p, 9p, 12p, 15q, 16p, Xq, Yq | 414 | 30 | 16 | telomere-subtelomere |
| Capan-2 | 12 | Xq, Yq, 1p, 4p, 9p, 16p | 1p, 9p, 12p, 15q, 16p, Xq, Yq | 294 | 31 | 17 | telomere-subtelomere |
| Capan-2 | 1 | Xq, Yq, 1p, 4p, 9p, 16p | 1p, 9p, 12p, 15q, 16p, Xq, Yq | 571 | 71 | 18 | telomere-subtelomere |
| CFPAC-1 | 3 | 4q, 5q | 12p | 61 | 3 | 19 | telomere-subtelomere |
| HPDE | 1 | 4p, 16p | 12p | 157 | 7 | 20 | telomere-subtelomere |
| Hs766T | 2 | 8p* | 1p, 9p, 15q, 12p, Xq, Yq | 116 | 10 | 21 | telomere-subtelomere |
| Hs766T | 1 | 8p* | 15q | 124 | 12 | 22 | telomere-subtelomere |
| Panc05.04 | 2 | Xq, Yq, | 1p, 9p, 15q, 12p, Xq, Yq | 216 | 18 | 23 | telomere-subtelomere |
| Panc05.04 | 6 | Xq, Yq, | 1p, 9p, 15q, 12p, Xq, Yq | 264 | 19 | 24 | telomere-subtelomere |
| Panc05.04 | 8 | Xq, Yq, | 1p, 9p, 15q, 12p, Xq, Yq | 417 | 22 | 25 | telomere-subtelomere |
| Panc08.13 | 4 | 4q, 22q | 16p | 206 | 14 | 26 | telomere-subtelomere |
| Panc08.13 | 2 | 4q, 22q | 16p | 235 | 16 | 27 | telomere-subtelomere |
| Panc08.13 | 5 | 4q, 22q | 16p | 394 | 23 | 28 | telomere-subtelomere |
| Panc10.05 | 5 | Xq, Yq | 1p, 9p ,12p | 141 | 17 | 29 | telomere-subtelomere |
| Panc10.05 | 1 | 4q, 5q | 1p, 9p, 15q | 124 | 14 | 30 | telomere-subtelomere |
| Panc10.05 | 2 | Xq, Yq | 1p, 9p, 15q | 164 | 20 | 31 | telomere-subtelomere |
| Panc10.05 | 3 | 4q, 5q | Xq, Yq | >170 | N/A | | telomere-telomere |
| PANC198 | 18 | 1p, 9p, Xq, Yq | 1p, 9p, 12p, 15q, Xq, Yq | 656 | 49 | 32 | telomere-subtelomere |
| Panc2.8 | 6 | 12q | 1p, 9p, 12p, 15q, 16p, Xq, Yq | 160 | 8 | 33 | telomere-subtelomere |
| Panc2.8 | 2 | 1q, 22q | 1p, 9p, 15q | 391 | 43 | 34 | telomere-subtelomere |
| Panc2.8 | 3 | 1q, 22q | 1p, 9p, 15q | 606 | 67 | 35 | telomere-subtelomere |
| PANC215 | 8 | 2q | 1p, 9p, 15q | 137 | 6 | 36 | telomere-subtelomere |
| PANC215 | 2 | 2q | 1p, 9p, 15q | 144 | 7 | 37 | telomere-subtelomere |
| PANC215 | 1 | 1q, 2q, 4q, 5q, 6q, 10q, 13q, 22q | 1p, 9p, 15q | 204 | 22 | 38 | telomere-subtelomere |
| Panc3.014 | 4 | 1p, 9p | 1p, 9p, 12p, 15q, Xq, Yq | 198 | 16 | 39 | telomere-complex |
| PANC486 | 3 | 1q, 22q | 1p, 9p, 15q | 147 | 16 | 40 | telomere-subtelomere |
| PANC486 | 6 | 8p | 1p, 9p, 15q | 212 | 20 | 41 | telomere-subtelomere |
| PANC486 | 4 | 1q, 22q | 1p, 9p, 15q | 271 | 24 | 42 | telomere-complex |

TABLE 1-continued

Telomere fusion junction sequence analysis of pancreatic cancer cell lines and HPDE.

| Cell line | Clone ID | Fusion chromosomes A | Fusion chromosomes B | Telomeric repeat length (nt) | (TTAGGG)n | SEQ ID NO: | Fusion pattern (fusion chromosome A-B) |
|---|---|---|---|---|---|---|---|
| PK-8 | 1 | 1q, 22q | 1p, 15q | 129 | 2 | 43 | telomere-subtelomere |
| PK-8 | 31 | 1q, 21q, 22q | 1p, 15q | 118 | 3 | 44 | telomere-subtelomere |
| PK-8 | 0 | 1q, 21q, 22q | 1p, 15q | 471 | 37 | 45 | telomere-subtelomere |
| PK-9 | 3 | 2q | 1p, 9p, 12p, 15q, 16p, Xq, Yq | 137 | 6 | 46 | telomere-subtelomere |
| PL11 | 6 | 10q | 1p, 9p, 15q | 124 | 10 | 47 | telomere-subtelomere |
| PL4 | 11 | 1p, 9p | 1p, 9p, 12p, 15q, Xq, Yq | 77 | 1 | | telomere-subtelomere |
| PL8 | 2 | 4q, 5q | 1p, 9p, 15q | 77 | 7 | 48 | telomere-subtelomere |
| PL8 | 8 | 16p | 16p | 99 | 13 | 49 | telomere-subtelomere |
| SU.86.86 | 2 | 1q | 12p | 464 | 53 | 50 | telomere-complex |
| SW1990 | 3 | 1p, 9p, Xq, Yq | 1p, 9p, 12p, 15q, 16p, Xq, Yq | 60 | 1 | | telomere-subtelomere |
| SW1990 | 2 | 1q, 22q | 1p, 9p, 12p, 15q, 16p, Xq, Yq | 115 | 13 | 51 | telomere-subtelomere |

*Chromosomal arm 8p fusion detected by 1 base misannealing of q-subtel 2 primer.
**Chromosomal arm 12q fusion detected by 2 base misannealing of q-subtel 2 primer.

As expected, all qPCR positive cell lines had subtelomeric sequences with TTAGGG repeats. FIG. 5D shows a representative example of a fusion junction sequence from AsPC-1 cells. FIG. 5E shows almost of the PL4 fusion contained variant repeat sequences (TGAGGG, TGGGGG, TTGGGG, and TTCGGG). Among the 23 fusion-positive cell lines, 20 cell lines had a telomere-subtelomere fusion, i.e. the fusion of a very short telomeric repeat from one chromosomal end to a subtelomere region without any telomeric repeats from the other chromosomal end (Table 1, FIG. 2A).

Three cell lines (SU.86.86, Panc 3.014 and PANC 486) had fusions containing small insertions between the telomeric repeats of one chromosome and the subtelomere of the other (complex telomere-fusions) (Table 1, FIG. 2A). FIG. 6 shows an example of a complex fusion junction found in PANC 486 cells. Some cell lines had multiple different fusions (47 unique clones were identified) (Table 1) as has been shown previously in other tumor types.

The inventors also performed the fusion assay on DNA from 60 pancreatic cancer xenograft samples. A summary of these cases is provided in Table 2.

SUPPLEMENTARY TABLE S3

Patient and pathology information for pancreatic cancer xenografts

| Sex, n (%) | |
|---|---|
| Male | 31 (51.7) |
| Female | 29 (48.3) |
| Age, median (range), year | 70 (38-90) |
| Tumor site, n (%) | |
| head/uncinate process | 48 (80.0) |
| body | 4 (6.7) |
| tail | 8 (13.3) |

SUPPLEMENTARY TABLE S3-continued

Patient and pathology information for pancreatic cancer xenografts

| Histological diagnosis, n (%) | |
|---|---|
| adenocarcinoma | 54 (90.0) |
| adenosquamous carcinoma | 3 (5.0) |
| adenocarcinoma arising from IPMN | 3 (5.0) |
| Histological differentiation, n (%) | |
| G1 | 0 (0.0) |
| G2 | 26 (43.3) |
| G2-G3 | 3 (5.0) |
| G3 | 30 (50.0) |
| G4 | 1 (1.7) |
| Tumor size, median (range), cm | 4.0 (2.0-6.0) |
| Primary tumor factor, n (%)* | |
| T1 | 4 (6.7) |
| T2 | 40 (66.7) |
| T3 | 13 (21.6) |
| T4 | 3 (5.0) |
| Regional lymph node metastasis, n (%)* | |
| N0 | 10 (16.7) |
| N1 | 24 (40.0) |
| N2 | 26 (43.3) |
| Telomere fusion status, n (%) | |
| Fusion positive | 34 (56.7) |
| Fusion negative | 26 (43.3) |

*Determined by AJCC classification ($8^{th}$ edition)

Figure 8:
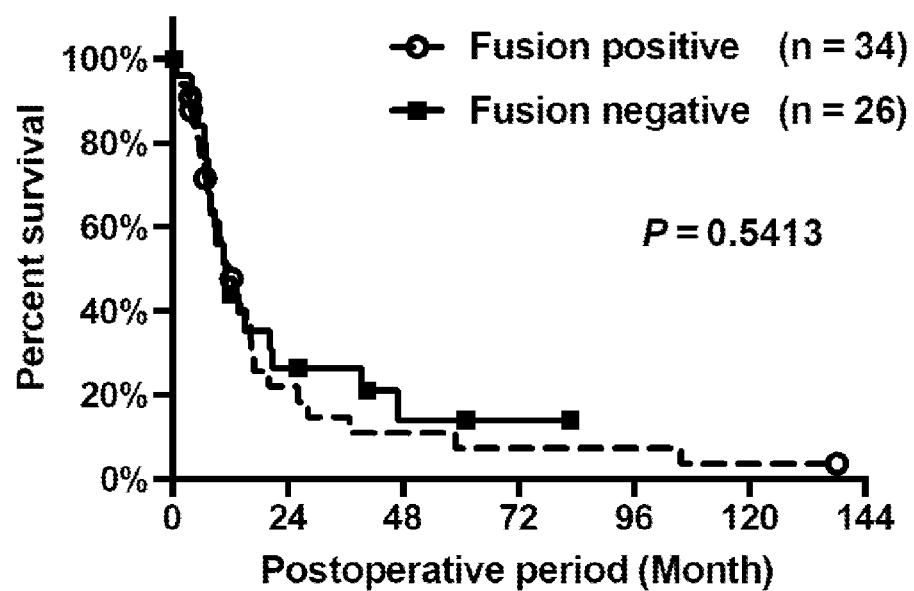
FIG. 8 illustrates Kaplan-Meier curve of overall survival characterized by telomere fusion status in pancreatic cancer xenograft samples. Patients lost to follow up were censored at their last visit.

Overall, 34 of the 60 (56.7%) pancreatic cancer xenografts were fusion positive. FIG. 7 shows representative examples of fusions detected in pancreatic cancer xenografts. No fusions were detected in mouse DNA (mouse telomeres have the same hexametric TTAGGG repeat sequence as humans (FIG. 7C). There was no the significant association between tumor pathology (i.e. tumor size, lymph node metastasis, and histological differentiation) and telomere fusion status (Table 3) and survival of patients was similar irrespective of the fusion status of their pancreatic cancer (P=0.54, FIG. 8)

TABLE 3

Characteristics of the telomere fusion positive and negative pancreatic cancer cases.

| Features | Fusion negative (n = 26) | Fusion positive (n = 34) | P |
|---|---|---|---|
| Age, median (range) | 66 (49-89) | 67.5 (38-90) | 0.638 |
| Sex, n | | | |
| Male | 12 | 19 | 0.600 |
| Female | 14 | 15 | |
| Histological differentiation, n* | | | |
| G1-G2 | 10 | 16 | 0.990 |
| G3-G4 | 13 | 18 | |
| Tumor size, n | | | |
| ≤4.0 cm | 22 | 23 | 0.230 |
| >4.0 cm | 4 | 11 | |
| N stage, n** | | | |
| N0 | 5 | 5 | 0.079 |
| N1 | 14 | 10 | |
| N2 | 7 | 19 | |

*Three cases did not have available histological grade information.
**Determined by AJCC classification (8th edition)

To better estimate the amount of cancer DNA required to identify a fusion with our assay, we performed the fusion assay using lower amounts of input DNA from several fusion positive and negative cells lines. Fusions were detected in four fusion-positive cell lines using 10 ng of input DNA, but fusions were not detected reliably using lower amounts of DNA below this amount (Supplementary Table S4). To exclude PCR efficiency as an explanation for our results, we quantified telomere fusion PCR products of two different fusion amplicons using a Bioanalyzer and spiked these PCR products into wild-type DNA and determined how many amplicons were required to get amplification. After obtaining fusion products generated from performing the $1^{st}$- and $2^{nd}$-round PCR on cancer cell lines that consistently generated fusions, the spiked fusion amplicons could be amplified using the $3^{rd}$ round PCR at concentrations as low as one amplicon. Similar results were obtained when fusion amplicons were generated with two rounds of the $1^{st}$-round PCR (30 cycles each); fusion amplicons could be detected using the $2^{nd}$ round PCR at amplicon concentrations of ~1 amplicon per sample (data not shown). These results indicate that PCR efficiency is not the primary reason for the inability to amplify telomere fusions with low amounts of input DNA.

Figure 9:
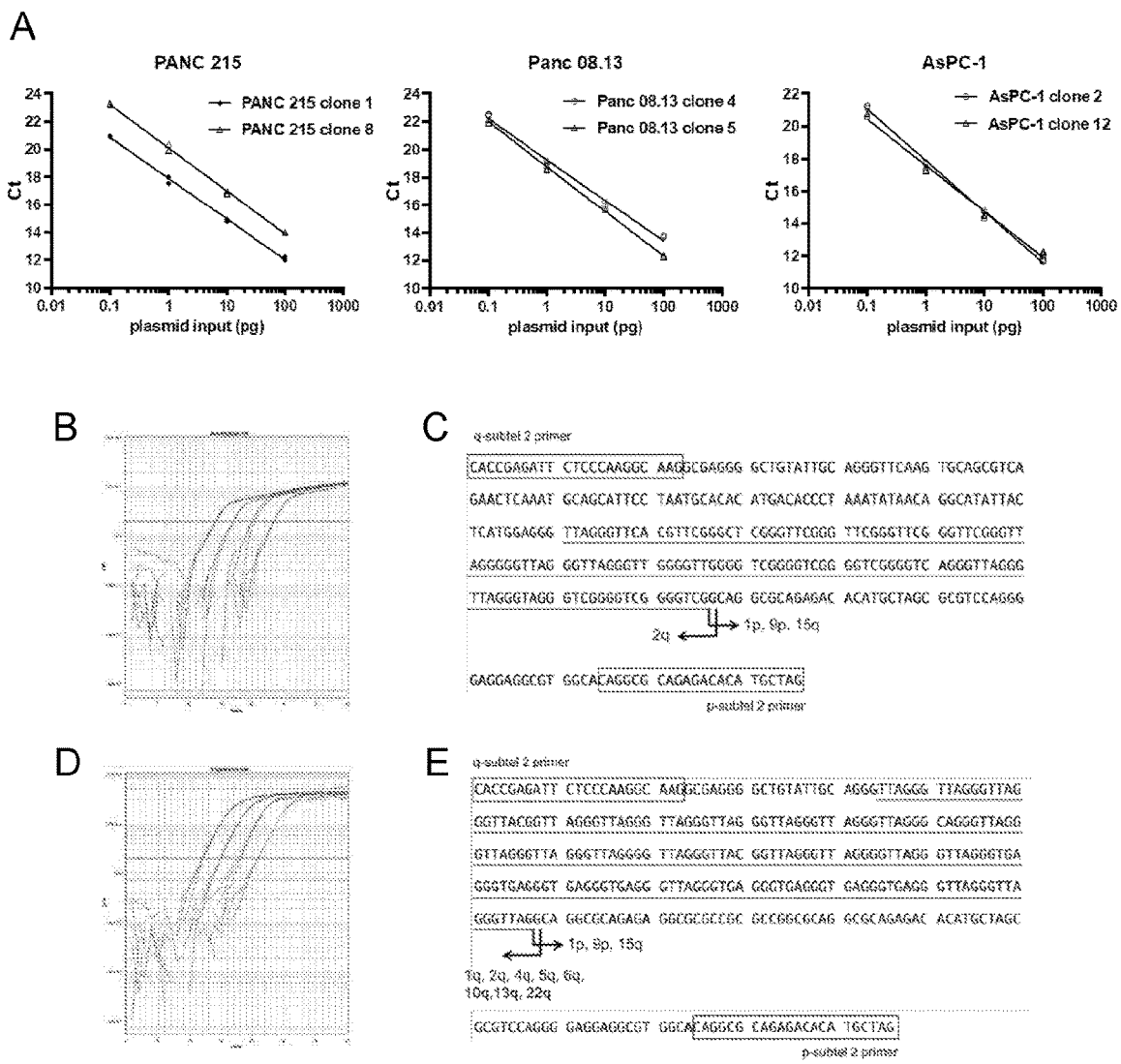
FIG. 9A-9E illustrates Nested-qPCR performance using various telomere fusion junction sequences as templates. (A) Standard curve of serially diluted DNA for all tested clones. (B, C) Amplification curve of serially diluted DNA (B) and fusion junction sequence (C) of PANC 215 clone 8 (SEQ ID NO: 78). (D, E) Amplification curve of serially diluted DNA (D) and fusion junction sequence (E) of PANC 215 clone 1 (SEQ ID NO: 79). Open rectangle indicates primer sequence and telomeric repeats were underlined.

Telomere fusion sequences had a variable number of telomeric repeats including in some cases the presence of telomere variant sequences (Table 1). Most fusions had variant repeat sequences; the presence of variant repeats is thought to contribute to telomere dysfunction and fusion formation. Most telomere fusion variant sequences involved substitutions consistent with nucleotide misincorporation that arise when telomerase performs telomere extensions. The inventors examined how quantification by the qPCR assay was affected by the number of telomere repeats in the telomere fusions. The inventors used cloned plasmid DNA from PANC 215, Panc 08.13, and AsPC-1 cells, and found clones with more TTAGGG repeats generated lower Ct values than clones with fewer repeats (Table 1, FIGS. 9A and 9B). Amplification of PANC 215 (clone 8), which generated a higher Ct value had only six TTAGGG repeats (SEQ ID NO: 82) in the fusion and they were not present as a continuous [TTAGGG]$_4$ (SEQ ID NO: 7) repeat; instead one or more TTAGGG repeats were dispersed throughout the fusion junction with intervening variant sequences such as TTCGGG, TCGGGG, and TTGGGG which resulted in atypical amplification curve (FIGS. 9C and 9D), unlike the linear amplification observed for PANC 215 (clone 1) fusion (FIGS. 9E and 9F). Other telomere-fusion positive DNA samples with atypical variant repeat sequences were also identified using the [TTAGGG]$_4$ (SEQ ID NO: 7) probe; many of these samples also had the [TTAGGG]4 (SEQ ID NO: 7) target sequence, and others may have been identified because there was sufficient annealing of the [TTAGGG]$_4$ (SEQ ID NO: 7) for detection. These results indicate that Ct values are affected by both the number of fusion templates in a samples and by the number and sequence of the telomeric repeats within the fusion junction.

Telomere length and telomere fusions in pancreatic cancer cell lines

Figure 10:
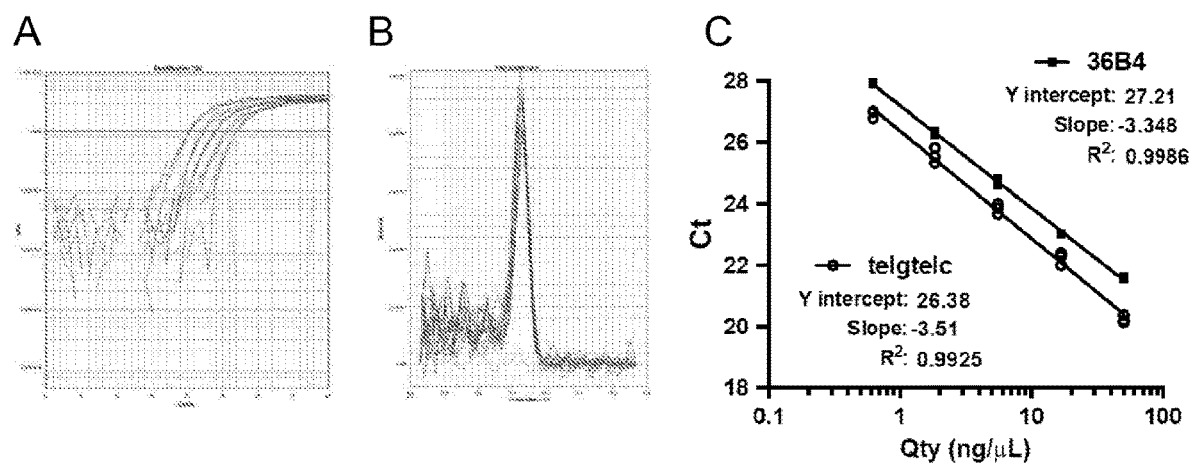
FIG. 10A-10C illustrates validation of telomere length measurement assay using qPCR technique. (A) Amplification curves using telomere telg/telc primers and serially diluted human genomic DNA. (B) Dissociation curves of single product amplifications using telg/telc primers. (C) Standard curves for telomeric repeat length and single copy reference (36B4).
Figure 11:
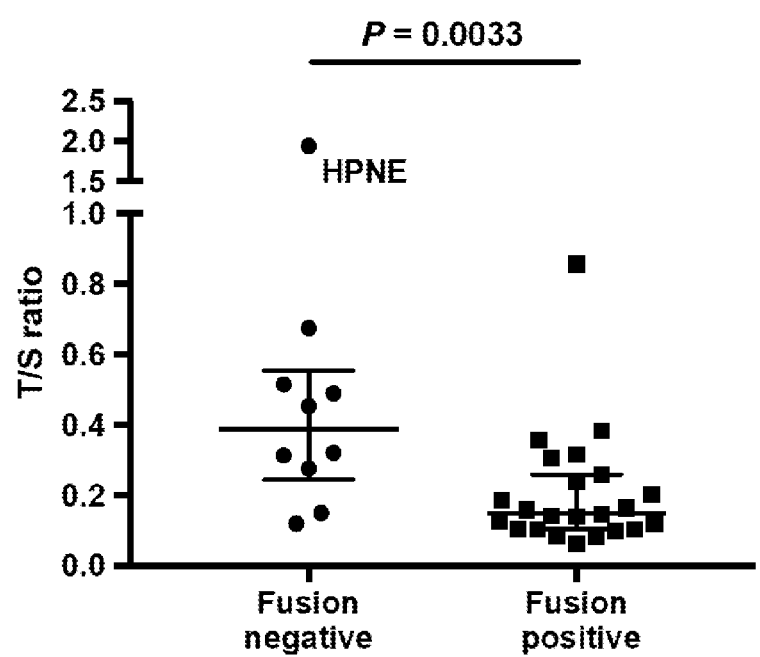
FIG. 11 illustrates telomere lengths measured in 31 pancreatic cancer cell lines and HPDE and HPNE cells classified by their telomere fusion status. The longer horizontal bar represents the median value and shorter ones represents values of the 75th and 25th percentiles, respectively.
Figure 12:
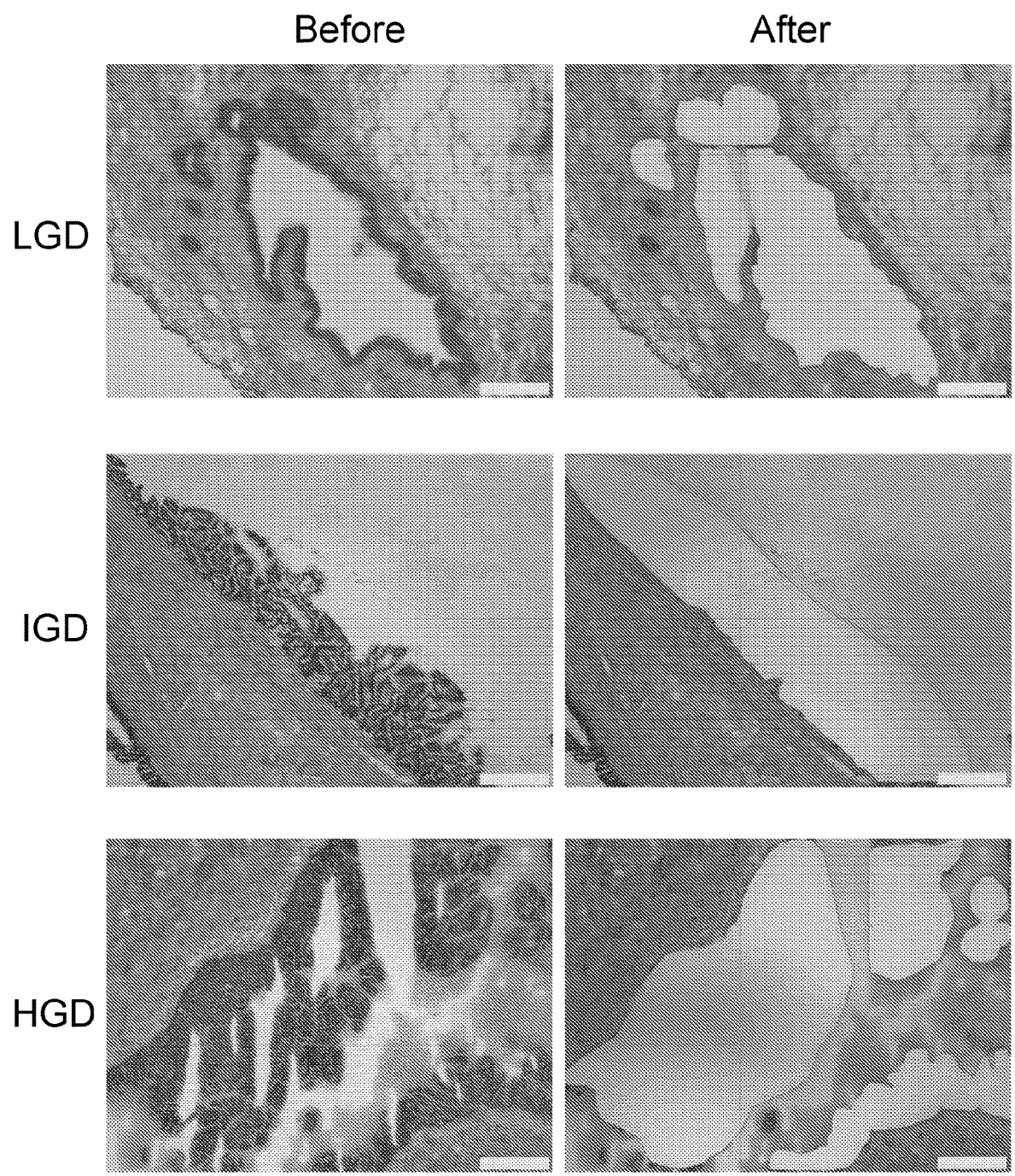
FIG. 12 illustrates representative H and E images of IPMN frozen sections before and after LCM. Scale bars: 400 μm.

Since telomere fusions are thought to be more likely to occur in cells with critically short telomeres, we examined the association between telomere length and the telomere fusion. The telomere length assay was evaluated for its specificity, linearity and reproducibility (FIG. 10). We found that fusion-positive pancreatic cancer cell lines had significant shorter telomere length than fusion-negative cell lines (P=0.0033) (FIG. 11).

Telomere fusion detection and telomere length measurement in IPMN tissue samples We next performed the fusion assay on DNA isolated from IPMN, normal pancreas and normal duodenum. No fusions were detected in 39 normal pancreas and duodenal tissue samples. We then analyzed 93 laser capture microdissected IPMNs of different histologic grades along with adjacent normal pancreas tissue obtained from the same tissue sections. A summary of the description of the IPMN cases is provided in Table 4 and representative examples of IPMN tissue before and after LCM is provided in Table 5.

TABLE 4

Patient information for the 93 primary IPMN cases

| Characteristics | Total (n = 93) | LGD (n = 19) | IGD (n = 49) | HGD (n = 25) | P |
|---|---|---|---|---|---|
| Sex (n) | | | | | |
| Male | 53 | 8 | 25 | 20 | 0.020* |
| Female | 40 | 11 | 24 | 5 | |
| Age, median (range), year | 60.5 (27-87) | 59 (46-82) | 69 (44-85) | 65 (27-87) | 0.298** |
| Race/ethnicity (n) | | | | | |
| African American | 2 | 0 | 1 | 1 | ND |
| Caucasian | 83 | 17 | 42 | 24 | |
| Asian | 3 | 1 | 2 | 0 | |
| Others, unknown | 5 | 1 | 4 | 0 | |

Figure 3:
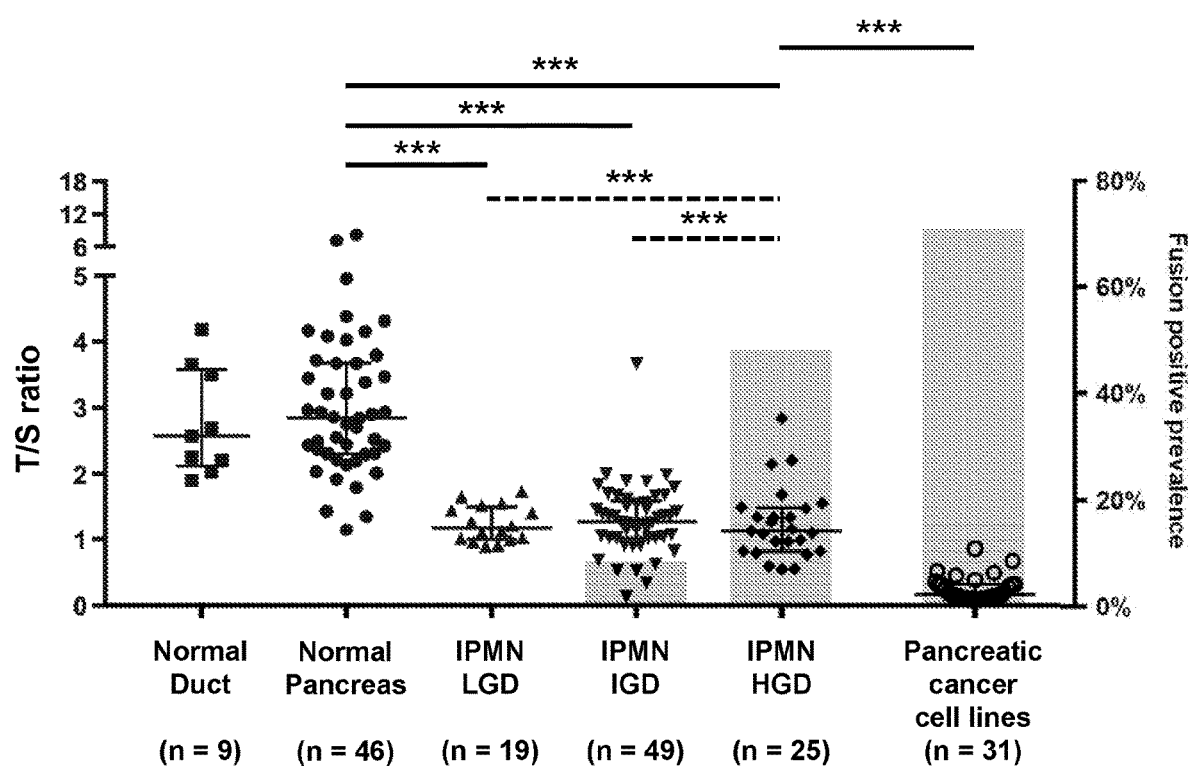
FIG. 3 characterizes telomere fusions and telomere length in normal and IPMN tissues. Scatter plot graph with left Y axis indicates telomere length. The longer horizontal bar represents the median value and shorter ones represents values of the 75th and 25th percentiles, respectively. Gray-color bar graph with right Y axis indicates telomere fusion prevalence. Solid horizontal lines represent the comparison of telomere lengths and the dashed line represents the comparison of telomere fusion prevalence. There was insufficient DNA available from three LGD cases for telomere length analysis. *P<0.001 FIG. 4A-4C Telomere fusions detected in IPMN cyst fluid samples. (A) The prevalence of telomere fusions in IPMN cyst fluid samples according to their grade of dysplasia. (B) Cyst fluid telomerase activity. The longer horizontal bar represents the median value and shorter ones represents values of the 75th and 25th percentiles, respectively. Red color dots indicate fusion positive samples. (C) Telomerase activities in cyst fluid samples with or without telomere fusions. INV, invasive cancer P<0.010, ***P<0.001

LGD, low-grade dysplasia;
IGD, intermediate-grade dysplasia;
HGD, high-grade dysplasia;
ND, not done.
*Fisher exact test.
**One-way ANOVA Notably, telomere fusions were predominantly detected in IPMNs of higher histologic grades; 12 of 25 (48.0%) IPMN with HGD and 4 of 49 (8.2%) IPMN with IGD (FIG. 3). No telomere fusions were detected in 19 IPMN with LGD. The prevalence of telomere fusions in the IPMN cases with HGD was significantly higher than in those with IGD and LGD (both P<0.001). No fusions were detected in DNA from available adjacent normal pancreas tissue microdissected from 46 of these cases (FIG. 3). Some cases had multiple fusions detected (only those with HGD). Representative results of fusion assay using IPMN cases are shown in FIG. 13.

The inventors next estimated the intra- and inter-assay variability of the fusion assay using representative fusion-positive tissue and cell line samples. FIGS. 14A and 14B shows the intra-assay variation of Ct values of four technical replicates (the coefficient of variation varied between 0.23 and 2.35%). Similar results were obtained when estimating the inter-assay variation by running independent assays on fusion-positive and fusion-negative samples on three different days (FIG. 14C).

The inventors also measured the telomere lengths of DNA from IPMNs and adjacent normal pancreas samples. As expected, IPMN cases of all histologic grades had significantly shorter mean telomere length than normal pancreas (FIG. 3). The telomere length of microdissected normal pancreas tissue DNA (n=46) and that of normal pancreatic ductal cells (n=9) were similar (FIG. 3). We compared the mean telomere length of IPMN samples and samples of adjacent normal pancreas from the same individuals. Mean telomere length was significantly shorter in IPMNs of all grades compared to adjacent normal pancreas (FIG. 15A) but there was no difference in the mean telomere length of fusion-positive compared to fusion-negative IPMNs (FIGS. 15B, 15C) or within the three histologic grades of IPMN (FIG. 15D). The average telomere length of IPMN DNA was significantly higher than that of pancreatic cancer cell lines (data not shown).

The inventors cloned and sequenced fusion-positive PCR products from 16 fusion-positive IPMN samples to isolate specific fusion junctions (Table 5). Fifteen of the 16 fusions were subtelomere-telomere fusions, i.e. telomeric repeats from one chromosomal end were fused to the subtelomere sequence of another chromosome (FIG. 2A, Table 5). One IPMN (a case with IGD) had an interstitial fusion; i.e. shortened telomeric repeats from one chromosomal end fused to a broken 2q arm that had ancestral interstitial telomeric repeats integrated within chromosome 2q13-q14.1 (Table 5).

TABLE 5

Telomere fusion junction sequence analysis of IPMN tissues.

| Sample | Clone ID | Grade of dysplasia | Fusion chromosomes A | Fusion chromosomes B | Telomeric repeat length (nt) | (TTAGGG)n | SEQ ID NO: | Fusion pattern (fusion chromosome A-B) |
|---|---|---|---|---|---|---|---|---|
| 104T | 7 | IGD | 4q, 5q, 22q | 12p | 61 | 3 | 52 | telomere-subtelomere |
| 154T | 4 | IGD | 4p, 16p, 16q, 19p | 2q13 | >220 | N/A | | telomere-non chromosomal end |
| 284T | 16 | HGD | 4q, 5q | 1p, 9p, 12p | 77 | 6 | 53 | telomere-subtelomere |
| 284T | 8 | HGD | 4q, 5q | 12p | 61 | 3 | 54 | telomere-subtelomere |
| 303T | 3 | HGD | 4q, 22q | 12p | 235 | 14 | 55 | telomere-subtelomere |
| 411T | 1 | HGD | 8p* | 1p, 9p, 12p, 15q, Xq, Yq | 98 | 10 | 56 | telomere-subtelomere |
| 414T | 5 | HGD | 4p, 16p, 16q, 19p | 1p, 9p, 12p, 15q, Xq, Yq | 327 | 28 | 57 | telomere-subtelomere |
| 414T | 4 | HGD | Xq, Yq | 1p, 9p, 12p, 15q, Xq, Yq | 302 | 28 | 58 | telomere-subtelomere |
| 443T | 2 | HGD | 4q, 5q | 1p, 15q | 149 | 16 | 59 | telomere-subtelomere |
| 497T | 1 | HGD | 4p, 16p, 16q | 1p, 9p, 12p, 15q, 16p, Xq, Yq | 157 | 6 | 60 | telomere-subtelomere |
| 517T | 5 | HGD | 12q** | 1p, 9p, 15q | 131 | 11 | 61 | telomere-subtelomere |
| 543T | 5 | IGD | 4p, 16p, 16q | 1p, 9p, 12p, 15q, Xq, Yq | 48 | 0 | | telomere-subtelomere |
| 568T | 2 | HGD | 8p* | 15q | 98 | 10 | 62 | telomere-subtelomere |
| 596T | 2 | HGD | 4q, 22q | 16p | 235 | 15 | 63 | telomere-subtelomere |
| 685T | 11 | HGD | 4q, 5q, 22q | 1p, 9p, 15q | 173 | 21 | 64 | telomere-subtelomere |
| 685T | 13 | HGD | 4q, 5q | 1p, 9p, 12p, 15q, 16p, Xq, Yq | 54 | 2 | 65 | telomere-subtelomere |
| 685T | 5 | HGD | 4q, 22q | 16p | 229 | 15 | 66 | telomere-subtelomere |
| 692T | 1 | HGD | 1q, 22q | 12p | 137 | 5 | 67 | telomere-subtelomere |

TABLE 5-continued

Telomere fusion junction sequence analysis of IPMN tissues.

| Sample | Clone ID | Grade of dysplasia | Fusion chromosomes A | Fusion chromosomes B | Telomeric repeat length (nt) | (TTAG GG)n | SEQ ID NO: | Fusion pattern (fusion chromosome A-B) |
|---|---|---|---|---|---|---|---|---|
| 692T | 2 | HGD | 1q, 22q | 12p | 430 | 38 | 68 | telomere-subtelomere |
| 840T | 1 | HGD | 16p | 1p, 9p, 12p, 15q, 16p, Xq, Yq | 63 | 6 | 69 | telomere-subtelomere |
| 847T | 2 | IGD | 4p, 16p | 1p, 9p, 12p, 15q, 16p, Xq, Yq | 156 | 7 | 70 | telomere-subtelomere |

HGD, high-grade dysplasia;
IGD, intermediate-grade dysplasia.
*Chromosomal arm 8p fusion detected by 1 base misannealing of q-subtel 2 primer.
**Chromosomal arm 12q fusion detected by 2 base misannealing of q-subtel 2 primer.

Telomere fusions from IPMN cases contained a variety of telomeric repeat lengths (from 48 to 430 bp from 100 to 400 bp, from 200 to 300 bp) and TTAGGG repeats (from 0 to 38 repeats (SEQ ID NO: 71), from 5 to 35 repeats (SEQ ID NO: 72), from 10 to 30 repeats (SEQ ID NO: 73), from 20 to 30 repeats (SEQ ID NO: 74)), a more narrow distribution than was found in the pancreatic cancer cell lines (FIGS. 2B and 2C).

Telomere fusion detection in surgically aspirated cyst fluid samples

To investigate the utility of telomere fusion detection as a biomarker for predicting the grade of dysplasia of IPMNs, the inventors next performed the telomere fusion assay using 93 surgically-aspirated cyst fluid samples derived from resected IPMNs. The characteristics of these patients and their IPMNs are summarized in Table 6.

TABLE 6

Patient and IPMN cyst characteristics.

| Characteristics | N (Total 93) |
|---|---|
| Male/Female (n) | 48/45 |
| Age, median (range), year | 67 (43-88) |
| Race/ethnicity (n) | |
| AA/C/Asian/Others, unknown | 5/82/3/3 |
| Symptoms (n) | |
| Abdominal pain | 17 |
| Pancreatitis | 11 |
| Jaundice | 3 |
| Cyst location (n) | |
| Head and uncinate/body and tail | 56/37 |
| Cyst size, median (range), cm | 3.0 (0.6-10.0) |
| Mural nodule (n)* | |
| Absent/Present | 63/30 |
| Communication with MPD (n)* | |
| Absent/Present | 45/48 |
| Dilatation of MPD ≥ 10 mm (n)* | |
| Absent/Present | 75/18 |
| Dilatation of MPD ≥ 5 mm (n)* | |
| Absent/Present | 53/40 |
| Cyst fluid appearance (n) | |
| Serous/Mucinous | 57/36 |

TABLE 6-continued

Patient and IPMN cyst characteristics.

| Characteristics | N (Total 93) |
|---|---|
| CT/MRI findings | |
| High-risk stigmata | 28 |
| Worrisome features | 53 |
| No concerning features | 12 |
| Original cyst volume (median, range), μL | 200 (10-450) |
| Operative procedure (n) | |
| PD/DP/TP/MP | 58/31/2/2 |
| Morphological duct type (n)* | |
| Main duct/mixed/branch duct | 18/32/43 |
| Grade of dysplasia (n) | |
| LGD/IGD/HGD/INV | 9/39/26/19 |

Figure 4:
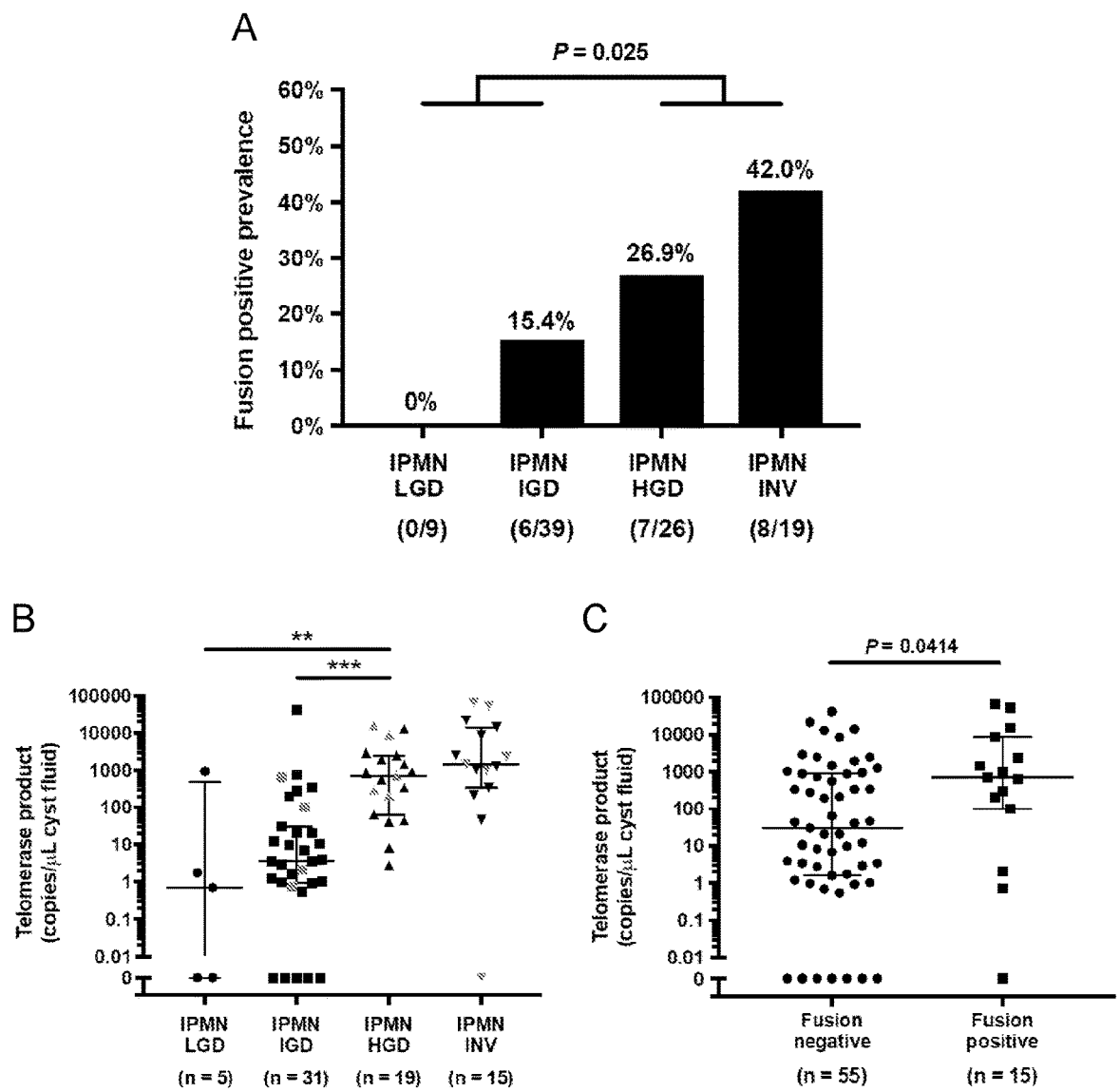

AA, African American;
C, Caucasian;
MPD, main pancreatic duct;
PD, pancreaticoduodenectomy;
DP, distal pancreatectomy;
TP, total pancreatectomy;
MP, middle pancreatectomy;
LGD, low-grade dysplasia;
IGD, intermediate-grade dysplasia;
HGD, high-grade dysplasia;
INV, invasive cancer.
*Determined by CT/MRI No fusions were detected in the cyst fluid samples from IPMNs with LGD (0 of 9, 0%) and the prevalence of detected telomere fusions increased with histologic grade: IGD (6 of 39, 15.4%) to HGD (7 of 26, 26.9%) and an associated invasive cancer (8 of 19, 42.9%) (FIG. 4A). The difference in the prevalence of telomere fusions in higher grade lesions (IPMNs with HGD and/or an associated invasive cancer) vs. lower grades (IPMN with IGD or LGD) was statistically significant (P=0.025). Using lower amounts of cyst fluid DNA to detect telomere fusions resulted in a lower rate of fusion detection (Table 7).

TABLE 7

Telomere fusion detection in IPMN cyst fluid samples according to input DNA

| Sample ID | KRAS mutant allele frequency (%)* | GNAS mutant allele frequency (%)* | Input DNA for fusion assay (ng/well) | | | |
|---|---|---|---|---|---|---|
| | | | 10.0 | 3.0 | 1.0 | 0.1 |
| 1 | 39.3 | 38.2 | + | − | − | − |
| 2 | 0.0 | 0.0 | + | − | − | − |
| 3 | 0.0 | 0.0 | + | − | − | − |
| 4 | 0.0 | 53.4 | + | + | − | − |
| 5 | 0.0 | 43.8 | + | + | + | − |
| 6 | 14.5 | 0.0 | + | + | − | − |
| 7 | 41.9 | 40.5 | + | − | − | − |
| 8 | 0.0 | 0.0 | + | − | − | − |

*Mutant allele frequencies of KRAS and GNAS gene were based on our unpublished data.
"+" means fusion positive and "−" means fusion negative.

The concentration of KRAS and GNAS mutant allele frequencies in these cyst fluid samples is provided for comparison. We did identify several cases in which fusions were detected in the IPMN but not in the patients corresponding cyst fluid. This suggests that for some cases more cyst fluid DNA might need to be sampled to detect fusions. Table 1 shows that the presence of telomere fusions in cyst fluid samples was independent of other predictive factors of malignancy (HGD/invasive cancer) by multivariate analysis (odds ratio, 6.229; 95% CI, 1.605-27.988).

We also examined the relationship between telomere fusion status and the telomerase activity of IPMN cyst fluids. Telomerase activity data was available from 70 cyst fluid samples and was associated with high-grade dysplasia as the inventors previously reported (FIG. 4B). Most but not all IPMNs with telomere fusions had high telomerase activity and vice versa. Telomere fusion-positive cases had higher telomerase activity on average than fusion-negative cases (FIG. 4C).

IPMN development telomere fusions are only commonly detected in IPMNs with high-grade dysplasia, a stage of tumor development where chromosomal abnormalities become prevalent. The inventors' telomere fusion assay was able to identify telomere fusions in 68% of pancreatic cancer cell lines and xenografts and in 48% of IPMNs with an associated invasive adenocarcinoma. Consistent with prior studies, the inventor's did not find telomere fusions in normal tissue. Pancreatic cancer cell lines with telomere fusions had even shorter telomeres than those without fusions consistent with evidence that telomere fusions occur once telomeres become critically short. The inventors also find that cyst fluids containing telomere fusions were more likely to have elevated levels of telomerase, consistent with our understanding that telomerase is induced in cells with critically shortened telomeres in order to overcome crisis.

Few studies have described the detection of telomere fusions in solid tumors in part because laborious methods such as Southern blotting have been employed to identify them. The assay of the present invention utilizes qPCR methods including a telomere repeat probe for assay specificity. Since the assay does not require laborious experimental procedures, it can be readily applied to diagnostic laboratories to detect telomere fusions in clinical samples.

The use of telomere fusions as a biomarker can provide additional information beyond that provided by existing biomarkers. Gene mutations are very useful for classifying the type of pancreatic cyst, and can be helpful at predicting the grade of dysplasia particularly when mutations associated with high-grade dysplasia are detected (such as mutations in TP53 or SMAD4), but these are present in <50% of such cases. The detection of chromosomal copy number alterations can help predict the neoplastic grade of a pancreatic cyst but sophisticated assays are required to detect these alterations in secondary fluids. Telomerase activity is promising biomarker for predicting the grade of dysplasia of an IPMN and although telomerase activity and telomere fusions emerge at a similar stage in IPMN development, these two biomarkers have complementary diagnostic utility.

Telomere fusions were not identified as clonal events in pancreatic cancer and IPMN samples and were detected in only a small fraction of genome equivalents (<1/1000), consistent with prior observations. Although telomere fusions that arise from critically short telomeres can cause chromosomal breakage fusion breakage cycles, most telomere fusions are not tolerated by the cell and represent transient events that arise in neoplastic cells before they die.

The telomere fusion assay was designed to detect relatively small fusion amplicons which is useful for certain biomarker applications. Since most telomere fusions arise at critically shortened telomeres, most of the fusions detected have very few telomere repeats. The use of the telomere repeat probe has the advantage that it increases the specificity of the assay; telomere fusions that do not contain telomere repeats can be detected with additional PCR and sequencing. The telomere fusion assay of the present invention cannot detect fusions that arise where the target subtelomeric region has been deleted. It should also be noted that although the assays of the present invention use qPCR, it is a qualitative not a quantitative assay since our assay starts with a first-round PCR; the qPCR probe improves the specificity of the assay by targeting telomere repeats. The detection of telomere fusions with our assay was also a function of the amount of input DNA. It may be the case that some neoplasms with very rare telomere fusion events could be identified by sampling more tumor DNA.

The present results indicate that telomere fusions may serve as a novel biomarker for predicting of the presence of HGD lesion within a cyst. Although patients in this study underwent surgical resection and therefore had defined histology, the results of analyses cannot be directly applied to patients who undergo surveillance without surgical resection. Therefore, prospective studies are needed to evaluate the diagnostic utility of using telomere fusion detection for patients undergoing EUS evaluation and pancreatic cyst fluid sampling.

The inventors observe telomere fusion events in most pancreatic ductal adenocarcinomas and in IPMNs with high-grade dysplasia where they are related to high telomerase activity and critically short telomeres. These telomere fusion events can be readily detected in pancreatic cyst fluid and are helpful for predicting the grade of dysplasia of IPMN.

Kits

Any of the compositions described herein may be comprised in a kit. In a non-limiting example, one or more primers of the present invention may be comprised in a kit.

The kits may comprise a suitably amount of one or more primers of the present invention and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the one or more primers of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The one or more primer composition(s) may be formulated into a syringeable composition. In which case, the container means may itself be a syringe, pipette, and/or other such like apparatus to apply to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES/METHODS

The following Examples/Methods have been included to provide guidance to one of ordinary skill in the art for practicing representative embodiments of the presently disclosed subject matter. In light of the present disclosure and the general level of skill in the art, those of skill can appreciate that the following Examples/Methods are intended to be exemplary only and that numerous changes, modifications, and alterations can be employed without departing from the scope of the presently disclosed subject matter. The following Examples/Methods are offered by way of illustration and not by way of limitation.

Tissues and Cyst Fluid Samples

IPMN tissues and cyst fluids were obtained from patients undergoing pancreatic resection at the Johns Hopkins Hospital from 2004 to 2015. IPMNs were identified at the time of frozen-section analysis of pancreatic resection specimens by a pathologist specializing in pancreas pathology (R.H.H.). Frozen sections of primary resected IPMN (n=93), any adjacent adenocarcinoma, and adjacent normal pancreas tissue were obtained from OCT blocks created in the surgical pathology suite shortly after the resection specimen was received and mounted onto membrane slides for subsequent laser capture microdissection. The collection and processing of surgical cyst fluid samples (n=93) has been described previously. Frozen tissue samples of normal pancreas (n=17) and duodenum (n=22) were obtained from pancreatic resection specimens after diagnostic evaluation from cases with non-malignant pancreatic disease including small localized pancreatic neuroendocrine tumors and serous cyst neoplasm. Genomic DNA was also isolated from 60 pancreatic cancer xenografts established from primary pancreatic adenocarcinomas resected from our institution as previously described. All elements of this study were approved by the Johns Hopkins Institutional Review Board, and written informed consent was obtained from all patients.

Cell Lines

Thirty-one human pancreatic cancer cell lines were examined. MIA PaCa-2, BxPC-3, Hs766T, PANC-1, AsPC-1, CFPAC-1, Capan-1, Capan-2, SU.86.86, HPAF-II, HPAC, and SW1990 were obtained from the American Type Culture Collection (Rockville, MD, USA). PK-8 and PK-9 cells are kind gifts from Dr. Akira Horii (Tohoku University, Sendai, Japan). Remaining cell lines were developed and maintained in our institution. An HPV-E6/E7 immortalized human pancreatic duct epithelial cell line, HPDE, was kindly provided by Dr. Ming-Sound Tsao (University of Toronto, Ontario, Canada). The generation and culture of hTERT-immortalized human pancreatic nestin-expressing (HPNE) cells has previously been described. These cancer cell lines were recently authenticated using genetic markers by the Johns Hopkins Genetics Core facility. HPDE was authenticated by testing it for genetic markers of HPV, E6 and E7. All cell lines, except for HPDE, were cultured in DMEM (Life Technologies, Inc.) supplemented with 10% FBS (Mediatech, Inc.) and 1% antibiotics (penicillin/streptomycin; Life Technologies) and incubated at 37° C. in a humidified atmosphere of 5% $CO_2$ in air. HPDE cells were cultured in keratinocyte serum-free medium supplemented by bovine pituitary extract and EGF (Life Technologies)

Laser Capture Microdissection (LCM)

Tissue sections were placed on ultraviolet-irradiated, membrane-coated slides (Carl Zeiss Microimaging, Munchen, Germany) and stored at −80° C. until needed. Slides were briefly stained with hematoxylin and eosin and were microdissected using an LCM system (Leica LMD7000; Leica, Buffalo Grove, IL). One frozen section slide was stained with hematoxylin and eosin as a guide.

DNA Extraction

Genomic DNA from microdissected tissues was extracted using the QIAamp DNA Micro Kit (QIAGEN, Germantown, MD). DNA was extracted from bulk tissue samples and surgically aspirated cyst fluid samples using DNeasy blood and tissue kit (QIAGEN). For cyst fluid samples with mucus, mucin was dissolved by increasing the length of proteinase K digestion. Whole-genome amplification was conducted for several cell line DNA samples with the REPLI-g Mini Kit (QIAGEN) using a 16 hour incubation time. All Extracted DNA was finally eluted with EB buffer (10 mM Tris-HCl, pH 8.5) and quantified using the Quantifiler Human DNA Quantification kit (Applied Biosystems, Foster City, CA).

Telomere Fusion Assay

Prior studies have used PCR to detect telomere fusions, but these assays were not been designed to detect these fusions in clinical samples such as cyst fluids. Since most telomere fusions contain very few telomere repeats, the inventors suspected that a telomere fusion PCR could be designed to amplify short telomere fusion amplicons for detection in clinical samples. The inventors designed primers to anneal to the subtelomere region close to (~100 bases from) telomeric repeat sequences. It is known that subtelomeric regions of many chromosomes have sequence homology. Thus, there is considerable homology between the (mostly) q arms 1q, 2q, 5q, 6q, 6p, 8p, 10q, 13q, 19p, 19q, 21q, 22q and 2q13, and between the p arms 1p, 9p, 12p, 15q 16p such that with one subtelomere q-arm PCR primer and one subtelomere p-arm PCR primer pair one could potentially amplify many different chromosomal end-to-end fusions.

Figure 1:
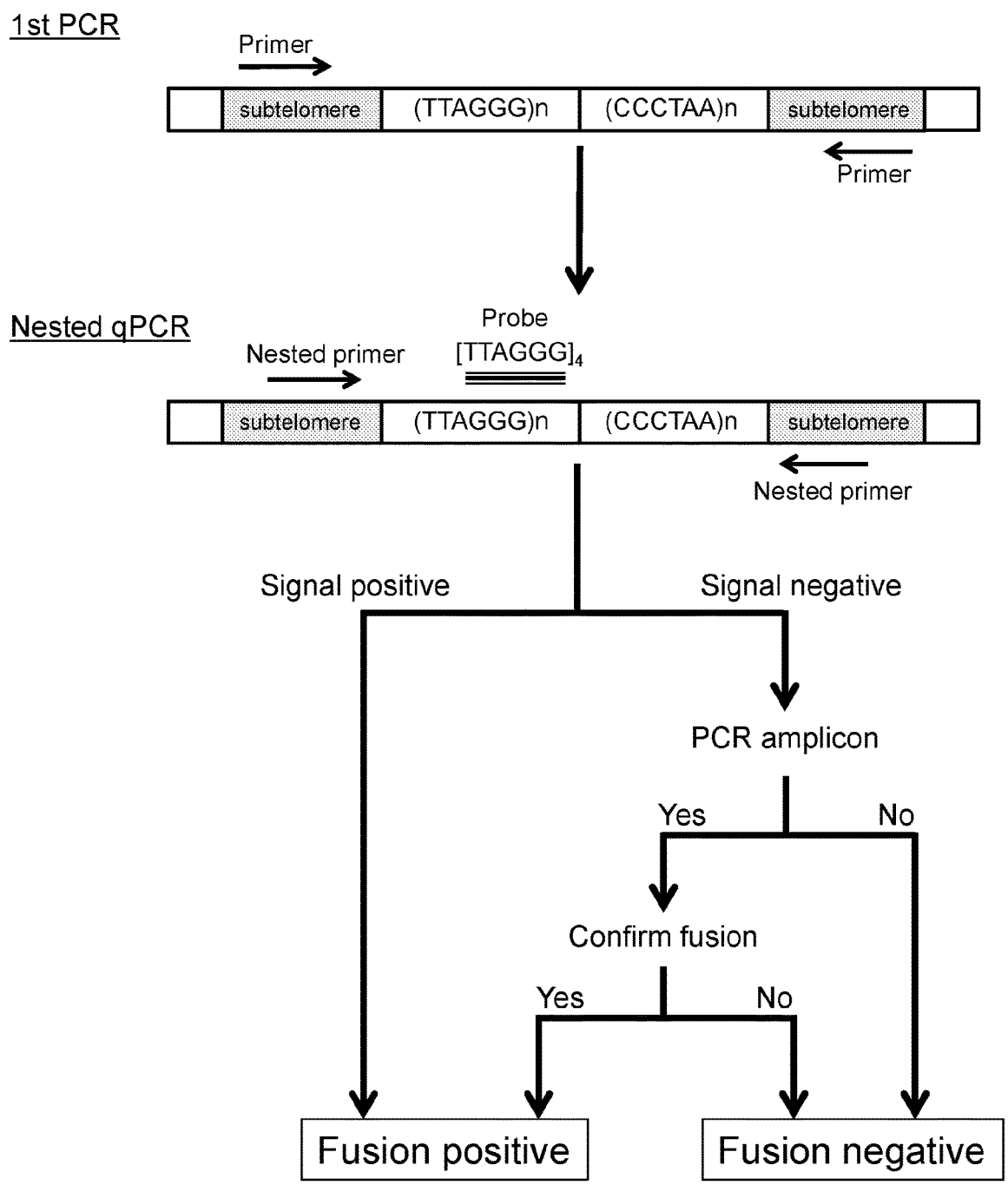
FIG. 1 illustrates an overview of an assay protocol of the present invention. "[TTAGGG]$_4$" is disclosed as SEQ ID NO: 7.

The inventors designed a nested-qPCR assay, with a first-round PCR that utilized a subtelomere q-arm PCR (q-subtel) primer targeting 1p, 1q, 2q, 4p, 4q, 5q, 6q, 9p, 10q, 13q, 16p, 16q, 19p, 21q, 22q, Xq, and Yq and a subtelomere p-arm PCR (p-subtel) primer that targeted the subtelomeric regions of 1p, 9p, 12p, 15p, 16p, Xq, and Yq, followed by a nested qPCR using PCR primers located internal to the first-round PCR primers and detected using a [TTAGGG]$_4$ (SEQ ID NO: 7) probe. An overview of the assay protocol is provided in FIG. 1. The first PCR was carried out in 10 μL with four replicates each containing 10 or 30 ng of genomic DNA, 1st primer set (500 nM of p-subtel 1 and q-subtel 1), 100 nM of 7-deaza-dGTP (New England Biolabs, Ipswich, MA), and Advantage GC genomic LA polymerase Mix (Clontech, Mountain View, CA). PCR conditions were 95° C. for 3 minutes (1 cycle), p-subtel and q-subtel primers used above) by employing primers targeting these subtelomeric regions in the first-round PCR followed by the nested qPCR assay with the [TTAGGG]$_4$ (SEQ ID NO: 7) probe. No telomere fusions were detected using the Xp or Yp primers (data not shown).

Primer and probe sequences used in this study are provided in Table 8.

TABLE 8

Primer and probe sequences used in this study.

| Primer | | Sequence 5'- -3' | Covered chromosomal arms |
|---|---|---|---|
| p-subtel 1 primer | 1st PCR | GACGCGCTAGCATGTGTCTCTG (SEQ ID NO: 1) | 1p, 9p, 12p, 15q, 16p, Xq, Yq |
| p-subtel 2 primer | Nested-qPCR, 3rd PCR | CTAGCATGTGTCTCTGCGCCTG (SEQ ID NO: 4) | |
| q-subtel 1 primer | 1st PCR | GAATCCTGCGCACCGAGATTCTC (SEQ ID NO: 2) | 1p, 1q, 2q, 4p, 4q, 5q, 6q, 9p, 10q, 13q, 16p, 16q, 19p, 21q, 22q, Xq, Yq |
| q-subtel 2 primer | Nested-qPCR | CACCGAGATTCTCCCAAGGCAAG (SEQ ID NO: 5) | |
| q-subtel 3 primer | 3rd PCR | CAAGGCAAGGSGAGGGGCTG (SEQ ID NO: 8) | |
| XpYp primer | 1st PCR | GGCTCAGGCAGTCTGCTTTTATTC (SEQ ID NO: 3) | Xp, Yp |
| XpYp primer | Nested-qPCR | CTCTAATCTGCTCCCACCCACATC (SEQ ID NO: 6) | |
| Probe | | Sequence 5'- -3' | |
| [TTAGGG]4 Probe | Nested-qPCR | /56-FAM/TTA+GGGTTA+GGGTTA+GGGTTA+GGG/3IABkFQ/ (SEQ ID NO: 7) | | followed by 30 cycles of 95° C. for 15 seconds, 60° C. for 30 seconds, 72° C. for 90 seconds. The PCR products from the four replicates were collected, pooled and diluted×100-fold. The nested-qPCR was conducted using a 7900HT thermocycler (Applied Biosystems) with 1 μL of first-round PCR diluted products, nested primers (500 nM of p-subtel2 and q-subtel2), 100 nM of 7-deaza-dGTP, Advantage GC genomic LA polymerase Mix, and 250 nM of locked nucleic acid (LNA) probe targeting the [TTAGGG]$_4$ (SEQ ID NO: 7) sequence with a 5' reporter dye (FAM) and 3' Iowa Black dark quencher (IABkFQ), synthesized by IDT (Integrated DNA Technologies, Inc., Coralville, IA). PCR conditions were 95° C. for 3 minutes (1 cycle), followed by 50 cycles of 95° C. for 15 seconds, 64° C. for 30 seconds, 72° C. for 45 seconds. The Ct is defined as the cycle number at which the fluorescence emission exceeds a fixed threshold (Delta Rn set as 2.0). A Ct of 35 was considered the lowest level of reliable detection. To identify fusion positive amplicons without [TTAGGG]$_4$ (SEQ ID NO: 7) repeats, nested-qPCR products were run in 0.8% agarose gels and amplicons of <1.0 kb that were not detected using the qPCR probe, were further characterized by applying another nested PCR to determine if these amplicons were true telomere fusions. Amplicons generated from this PCR were also subcloned and sequenced. This third-round PCR was carried out using× 300 dilution of nested-qPCR products and nested third-round primers (p-subtel 2 and q-subtel 3) with 71° C. annealing and 30 cycles.

We also employed the same nested qPCR approach in an attempt to detect fusions involving the subtelomeric region of the Xp and Yp chromosomal arms (with and without the Subcloning and sequencing of telomere fusion products Purified PCR products (using QIA quick Gel Extraction Kit, QIAGEN) were cloned into pCR 2.1-TOPO TA vector using TOPO TA Cloning Kit (ThermoFisher Scientific) following the manufacturer's instructions. White colonies on X-gal containing agar plate were chosen randomly for colony PCR selection and plasmid DNA extraction with QIAprep Spin Mini kit (QIAGEN) and sequenced using M13 F and R primers. Sequence analysis was carried out at The Johns Hopkins Synthesis & Sequencing Facility using automated DNA sequencers (Applied Biosystems). NCBI-BLAST of the telomere fusion sequences was used to identify the potential chromosomal arms involved.

Telomere Length Assay

Telomere length was determined as the relative ratio of telomere repeat copy number to a single copy gene copy number (T/S ratio) using real-time qPCR with minor modifications. Quantitative PCR was performed using QuantiTect SYBR Green PCR Master Mix (QIAGEN) using a 7900HT thermocycler (Applied Biosystems). Telomeric repeats were amplified using the following PCR conditions: initial denaturation at 95° C. for 10 min followed by 2 cycles of 94° C. for 15 sec and 49° C. for 15 sec, and then 40 cycles of 94° C. for 10 sec and 62° C. for 20 sec. The reference housekeeping gene 36B4 (known as ribosomal protein lateral stalk subunit P0) was amplified with following conditions: 95° C. for 10 min followed by 40 cycles of denaturation at 95° C. for 15 sec, and annealing and extension at 60° C. for 60 sec. To calculate the T/S ratios, each DNA standard curve was generated using commercialized human whole blood genomic DNA from multiple healthy anonymous donors (Promega, Madison, WI). We also calculated relative telomere erosion, the change in telomere length in tumor DNA compared to the matched adjacent normal tissue DNA. A ratio of <1 represents telomere shortening of tumor DNA. Primer sequences were described as previously.

Statistical Analysis

Non-parametric Mann-Whitney Utest was used to compare unpaired continuous variables. Wilcoxon matched-pairs signed rank test was used to compare paired continuous variables. Fisher exact test was used to compare categorical variables. Survival time was examined using the Kaplan-Meier method and compared using the log-rank test. A multivariate analysis was performed using the logistic regression model. All statistical analysis was performed using the JMP Pro 12.2.0 statistical software (SAS Institute Inc., Cary, NC, USA) and GraphPad Prism V7.0 (GraphPad Software, San Diego, CA, USA). P-value of less than 0.05 was considered to indicate statistical significance.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for detecting a telomere fusion in a clinical sample derived from an intraductal papillary mucinous neoplasm (IPMN) obtained from a subject comprising the steps of:
   (a) performing a first polymerase chain reaction (PCR) on deoxyribonucleic acid (DNA) present in the clinical sample using a first telomere primer set that hybridizes in the subtelomere region within about 100 nucleotides of telomeric repeat sequences, wherein the first telomere primer set comprises a subtelomere q-arm primer and a subtelomere p-arm primer, and wherein the first telomere primer set comprises SEQ ID NO:1 and/or SEQ ID NO:2;
   (b) performing a second nested PCR on the amplification products of step (a) using a second telomere primer set comprising SEQ ID NO:4 and/or SEQ ID NO:5; and
   (c) detecting a telomere fusion using a probe targeting SEQ ID NO:7.

2. A method for predicting high grade dysplasia (HGD) or invasive cancer in a patient comprising the steps of:
   (a) performing a first PCR on DNA present in a clinical sample derived from an IPMN using a first telomere primer set that hybridizes in the subtelomere region within about 100 nucleotides of telomeric repeat sequences, wherein the first telomere primer set comprises a subtelomere q-arm primer and a subtelomere p-arm primer, and wherein the first telomere primer set comprises SEQ ID NO:1 and/or SEQ ID NO:2;

(b) performing a second nested PCR on the amplification products of step (a) using a second telomere primer set comprising SEQ ID NO:4 and/or SEQ ID NO:5; and
(c) detecting a telomere fusion using a probe targeting SEQ ID NO:7,
wherein the detection of a telomere fusion likely indicates IPMN with HGD.

3. The method of claim 2, further comprising the step of performing surgical resection of the IPMN.

\* \* \* \* \*

SEQUENCE LISTING

```
<160> NUMBER OF SEQ ID NOS: 82

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacgcgctag catgtgtctc tg                                              22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaatcctgcg caccgagatt ctc                                             23

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggctcaggca gtctgctttt attc                                            24
```

```
<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctagcatgtg tctctgcgcc tg                                            22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccgagatt ctcccaaggc aag                                           23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctctaatctg ctcccaccca catc                                          24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttagggttag ggttagggtt aggg                                          24

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caaggcaagg sgaggggctg                                               20

<210> SEQ ID NO 9
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ttagggttag ggttagggtt agggttaggg ttagggttag ggttagggtt agggttaggg   60
ttagggttag ggttagggtt agggttaggg ttagggttag ggttagggtt agggttaggg  120
```

```
<210> SEQ ID NO 10
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
ttagggttag ggttagggtt agggttaggg ttagggttag ggttagggtt agggttaggg       60
ttagggttag ggttagggtt agggttaggg ttagggttag ggttagggtt agggttaggg      120
ttagggttag ggttagggtt agggttaggg ttagggttag ggttagggtt agggttaggg      180
ttaggg                                                                 186

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttagggttag ggttagggtt agggttaggg ttagggttag ggttagggtt agggttaggg       60

<210> SEQ ID NO 12
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ttagggttag ggttagggtt agggttaggg ttagggttag ggttagggtt agggttaggg       60
ttagggttag ggttagggtt agggttaggg ttagggttag ggttagggtt agggttaggg      120
ttagggttag ggttagggtt agggttaggg ttagggttag gg                         162

<210> SEQ ID NO 13
<211> LENGTH: 276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ttagggttag ggttagggtt agggttaggg ttagggttag ggttagggtt agggttaggg       60
ttagggttag ggttagggtt agggttaggg ttagggttag ggttagggtt agggttaggg      120
ttagggttag ggttagggtt agggttaggg ttagggttag ggttagggtt agggttaggg      180
ttagggttag ggttagggtt agggttaggg ttagggttag ggttagggtt agggttaggg      240
ttagggttag ggttagggtt agggttaggg ttaggg                                276

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 14
ttagggttag ggttagggg                                              18

<210> SEQ ID NO 15
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
ttagggttag ggtttagggtt agggttaggg ttagggttag ggtttagggtt agggttaggg    60 ttagggttag ggtttagggtt agggttaggg ttagggttag ggtttagggtt agggttaggg   120 ttagggttag ggtttagggtt agggttaggg ttagggttag ggtttagggtt agggttaggg   180 ttagggttag ggtttagggtt agggttaggg ttagggttag ggtttagggtt agggttaggg   240 ttagggttag ggtttagggtt agggttaggg ttagggttag ggtttagggtt agggttaggg   300 ttaggg                                                               306

<210> SEQ ID NO 16
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ttagggttag ggttagggtt agggttaggg ttagggttag ggttagggtt agggttaggg     60
ttagggttag ggttagggtt agggttaggg ttagggttag ggttagggtt agggttaggg    120
ttagggttag ggttagggtt agggttaggg ttagggttag ggttagggtt agggttaggg    180

<210> SEQ ID NO 17
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
ttagggttag ggttagggtt agggttaggg ttagggttag ggttagggtt agggttaggg     60
ttagggttag ggttagggtt agggttaggg ttagggttag ggttagggtt agggttaggg    120
ttagggttag ggttagggtt agggttaggg ttagggttag ggttagggtt agggttaggg    180
ttaggg                                                               186

<210> SEQ ID NO 18
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
ttagggttag ggttagggtt agggttaggg ttagggttag ggttagggtt agggttaggg     60
ttagggttag ggttagggtt agggttaggg ttagggttag ggttagggtt agggttaggg    120
ttagggttag ggttagggtt agggttaggg ttagggttag ggttagggtt agggttaggg        180
ttagggttag ggttagggtt agggttaggg ttagggttag ggttagggtt agggttaggg        240
ttagggttag ggttagggtt agggttaggg ttagggttag ggttagggtt agggttaggg        300
ttagggttag ggttagggtt agggttaggg ttagggttag ggttagggtt agggttaggg        360
ttagggttag ggttagggtt agggttaggg ttagggttag ggttagggtt agggttaggg        420
ttaggg                                                                   426

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ttagggttag ggttaggg                                                       18

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttagggttag ggttagggtt agggttaggg ttagggttag gg                            42

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttagggttag ggttagggtt agggttaggg ttagggttag ggttagggtt agggttaggg         60

<210> SEQ ID NO 22
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttagggttag ggttagggtt agggttaggg ttagggttag ggttagggtt agggttaggg         60
ttagggttag gg                                                             72

<210> SEQ ID NO 23
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
ttagggttag ggttagggtt agggttaggg ttagggttag ggttagggtt agggttaggg         60

```
ttagggttag ggttagggtt agggttaggg ttagggttag ggttaggg            108
```

<210> SEQ ID NO 24
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
ttagggttag ggttagggtt agggttaggg ttagggttag ggttagggtt agggttaggg    60
ttagggttag ggttagggtt agggttaggg ttagggttag ggttagggtt aggg         114
```

<210> SEQ ID NO 25
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
ttagggttag ggttagggtt agggttaggg ttagggttag ggttagggtt agggttaggg    60
ttagggttag ggttagggtt agggttaggg ttagggttag ggttagggtt agggttaggg   120
ttagggttag gg                                                      132
```

<210> SEQ ID NO 26
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

```
ttagggttag ggttagggtt agggttaggg ttagggttag ggttagggtt agggttaggg    60
ttagggttag ggttagggtt aggg                                          84
```

<210> SEQ ID NO 27
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
ttagggttag ggttagggtt agggttaggg ttagggttag ggttagggtt agggttaggg    60
ttagggttag ggttagggtt agggttaggg ttaggg                             96
```

<210> SEQ ID NO 28
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
ttagggttag ggttagggtt agggttaggg ttagggttag ggttagggtt agggttaggg    60
ttagggttag ggttagggtt agggttaggg ttagggttag ggttagggtt agggttaggg   120
```

```
ttagggttag ggttagggg                                              138

<210> SEQ ID NO 29
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
ttagggttag ggttagggtt agggttaggg ttagggttag ggttagggtt agggttaggg     60
ttagggttag ggttagggtt agggttaggg ttagggttag gg                       102

<210> SEQ ID NO 30
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttagggttag ggtagggtt agggttaggg ttagggttag ggttagggtt agggttaggg     60
ttagggttag ggttagggtt aggg                                            84

<210> SEQ ID NO 31
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
ttagggttag ggttagggtt agggttaggg ttagggttag ggttagggtt agggttaggg     60
ttagggttag ggttagggtt agggttaggg ttagggttag ggttagggtt agggttaggg    120

<210> SEQ ID NO 32
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
ttagggttag ggttagggtt agggttaggg ttagggttag ggttagggtt agggttaggg     60
ttagggttag ggttagggtt agggttaggg ttagggttag ggttagggtt agggttaggg    120
ttagggttag ggttagggtt agggttaggg ttagggttag ggttagggtt agggttaggg    180
ttagggttag ggttagggtt agggttaggg ttagggttag ggttagggtt agggttaggg    240
ttagggttag ggttagggtt agggttaggg ttagggttag ggttagggtt aggg          294

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
```

```
ttagggttag ggttagggtt agggttaggg ttagggttag ggttaggg            48

<210> SEQ ID NO 34
<211> LENGTH: 258
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
ttagggttag ggttagggtt agggttaggg ttagggttag ggttagggtt agggttaggg    60
ttagggttag ggttagggtt agggttaggg ttagggttag ggttagggtt agggttaggg   120
ttagggttag ggttagggtt agggttaggg ttagggttag ggttagggtt agggttaggg   180
ttagggttag ggttagggtt agggttaggg ttagggttag ggttagggtt agggttaggg   240
ttagggttag ggttaggg                                                 258

<210> SEQ ID NO 35
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ttagggttag ggttagggtt agggttaggg ttagggttag ggttagggtt agggttaggg    60
ttagggttag ggttagggtt agggttaggg ttagggttag ggttagggtt agggttaggg   120
ttagggttag ggttagggtt agggttaggg ttagggttag ggttagggtt agggttaggg   180
ttagggttag ggttagggtt agggttaggg ttagggttag ggttagggtt agggttaggg   240
ttagggttag ggttagggtt agggttaggg ttagggttag ggttagggtt agggttaggg   300
ttagggttag ggttagggtt agggttaggg ttagggttag ggttagggtt agggttaggg   360
ttagggttag ggttagggtt agggttaggg ttagggttag gg                      402

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttagggttag ggttagggtt agggttaggg ttaggg                             36

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttagggttag ggttagggtt agggttaggg ttagggttag gg                      42

<210> SEQ ID NO 38
<211> LENGTH: 132
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 38
ttagggttag ggttagggtt agggttaggg ttagggttag ggttagggtt agggttaggg     60
ttagggttag ggttagggtt agggttaggg ttagggttag ggttagggtt agggttaggg    120
ttagggttag gg                                                        132

<210> SEQ ID NO 39
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttagggttag ggttagggtt agggttaggg ttagggttag ggttagggtt agggttaggg     60
ttagggttag ggttagggtt agggttaggg ttaggg                               96

<210> SEQ ID NO 40
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttagggttag ggttagggtt agggttaggg ttagggttag ggttagggtt agggttaggg     60
ttagggttag ggttagggtt agggttaggg ttaggg                               96

<210> SEQ ID NO 41
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ttagggttag ggttagggtt agggttaggg ttagggttag ggttagggtt agggttaggg     60
ttagggttag ggttagggtt agggttaggg ttagggttag ggttagggtt agggttaggg    120

<210> SEQ ID NO 42
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
ttagggttag ggttagggtt agggttaggg ttagggttag ggttagggtt agggttaggg     60
ttagggttag ggttagggtt agggttaggg ttagggttag ggttagggtt agggttaggg    120
ttagggttag ggttagggtt aggg                                           144

<210> SEQ ID NO 43
<211> LENGTH: 12
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 43
ttagggttag gg                                                              12

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ttagggttag ggttaggg                                                        18

<210> SEQ ID NO 45
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
ttagggttag ggttagggtt agggttaggg ttagggttag ggttagggtt agggttaggg          60
ttagggttag ggttagggtt agggttaggg ttagggttag ggttagggtt agggttaggg         120
ttagggttag ggttagggtt agggttaggg ttagggttag ggttagggtt agggttaggg         180
ttagggttag ggttagggtt agggttaggg ttagggttag gg                            222

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttagggttag ggttagggtt agggttaggg ttaggg                                    36

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttagggttag ggttagggtt agggttaggg ttagggttag ggttagggtt agggttaggg          60

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttagggttag ggttagggtt agggttaggg ttagggttag gg                             42
```

<210> SEQ ID NO 49
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ttagggttag ggttagggtt agggttaggg ttagggttag ggttagggtt agggttaggg      60
ttagggttag ggttaggg                                                   78

<210> SEQ ID NO 50
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
ttagggttag ggttagggtt agggttaggg ttagggttag ggttagggtt agggttaggg      60
ttagggttag ggttagggtt agggttaggg ttagggttag ggttagggtt agggttaggg     120
ttagggttag ggttagggtt agggttaggg ttagggttag ggttagggtt agggttaggg     180
ttagggttag ggttagggtt agggttaggg ttagggttag ggttagggtt agggttaggg     240
ttagggttag ggttagggtt agggttaggg ttagggttag ggttagggtt agggttaggg     300
ttagggttag ggttaggg                                                  318

<210> SEQ ID NO 51
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttagggttag ggttagggtt agggttaggg ttagggttag ggttagggtt agggttaggg      60
ttagggttag ggttaggg                                                   78

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ttagggttag ggttaggg                                                   18

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ttagggttag ggttagggtt agggttaggg ttaggg                               36

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttagggttag ggttaggg                                                    18

<210> SEQ ID NO 55
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttagggttag ggttagggtt agggttaggg ttagggttag ggttagggtt agggttaggg      60
ttagggttag ggttagggtt aggg                                             84

<210> SEQ ID NO 56
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttagggttag ggttagggtt agggttaggg ttagggttag ggttagggtt agggttaggg      60

<210> SEQ ID NO 57
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
ttagggttag ggttagggtt agggttaggg ttagggttag ggttagggtt agggttaggg      60
ttagggttag ggttagggtt agggttaggg ttagggttag ggttagggtt agggttaggg     120
ttagggttag ggttagggtt agggttaggg ttagggttag ggttaggg                  168

<210> SEQ ID NO 58
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ttagggttag ggttagggtt agggttaggg ttagggttag ggttagggtt agggttaggg      60
ttagggttag ggttagggtt agggttaggg ttagggttag ggttagggtt agggttaggg     120
ttagggttag ggttagggtt agggttaggg ttagggttag ggttaggg                  168

<210> SEQ ID NO 59
<211> LENGTH: 96
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 59
ttagggttag ggttagggtt agggttaggg ttagggttag ggttagggtt agggttaggg    60
ttagggttag ggttagggtt agggttaggg ttaggg                              96

<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ttagggttag ggttagggtt agggttaggg ttaggg                              36

<210> SEQ ID NO 61
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ttagggttag ggttagggtt agggttaggg ttagggttag ggttagggtt agggttaggg    60
ttaggg                                                               66

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ttagggttag ggttagggtt agggttaggg ttagggttag ggttagggtt agggttaggg    60

<210> SEQ ID NO 63
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ttagggttag ggttagggtt agggttaggg ttagggttag ggttagggtt agggttaggg    60
ttagggttag ggttagggtt agggttaggg                                     90

<210> SEQ ID NO 64
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
ttagggttag ggttagggtt agggttaggg ttagggttag ggttagggtt agggttaggg    60
ttagggttag ggttagggtt agggttaggg ttagggttag ggttagggtt agggttaggg    120
ttaggg                                                              126

<210> SEQ ID NO 65
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ttagggttag gg                                                        12

<210> SEQ ID NO 66
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ttagggttag ggttagggtt agggttaggg ttagggttag ggttagggtt agggttaggg     60
ttagggttag ggttagggtt agggttaggg                                     90

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ttagggttag ggttagggtt agggttaggg                                     30

<210> SEQ ID NO 68
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
ttagggttag ggttagggtt agggttaggg ttagggttag ggttagggtt agggttaggg     60
ttagggttag ggttagggtt agggttaggg ttagggttag ggttagggtt agggttaggg    120
ttagggttag ggttagggtt agggttaggg ttagggttag ggttagggtt agggttaggg    180
ttagggttag ggttagggtt agggttaggg ttagggttag ggttaggg                228

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ttagggttag ggttagggtt agggttaggg ttaggg                              36

-continued

```
<210> SEQ ID NO 70
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ttagggttag ggttagggtt agggttaggg ttagggttag gg                        42

<210> SEQ ID NO 71
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(228)
<223> OTHER INFORMATION: This sequence may encompass 0-38 "ttaggg"
      repeating units

<400> SEQUENCE: 71
ttagggttag ggttagggtt agggttaggg ttagggttag ggttagggtt agggttaggg     60
ttagggttag ggttagggtt agggttaggg ttagggttag ggttagggtt agggttaggg    120
ttagggttag ggttagggtt agggttaggg ttagggttag ggttagggtt agggttaggg    180
ttagggttag ggttagggtt agggttaggg ttagggttag ggttaggg                 228

<210> SEQ ID NO 72
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(210)
<223> OTHER INFORMATION: This sequence may encompass 5-35 "ttaggg"
      repeating units

<400> SEQUENCE: 72
ttagggttag ggttagggtt agggttaggg ttagggttag ggttagggtt agggttaggg     60
ttagggttag ggttagggtt agggttaggg ttagggttag ggttagggtt agggttaggg    120
ttagggttag ggttagggtt agggttaggg ttagggttag ggttagggtt agggttaggg    180
ttagggttag ggttagggtt agggttaggg                                     210

<210> SEQ ID NO 73
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(180)
<223> OTHER INFORMATION: This sequence may encompass 10-30 "ttaggg"
      repeating units

<400> SEQUENCE: 73
ttagggttag ggttagggtt agggttaggg ttagggttag ggttagggtt agggttaggg     60
ttagggttag ggttagggtt agggttaggg ttagggttag ggttagggtt agggttaggg    120
```
ttagggttag ggttagggtt agggttaggg ttagggttag ggttagggtt agggttaggg      180

<210> SEQ ID NO 74
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(180)
<223> OTHER INFORMATION: This sequence may encompass 20-30 "ttaggg"
      repeating units

<400> SEQUENCE: 74
ttagggttag ggttagggtt agggttaggg ttagggttag ggttagggtt agggttaggg      60
ttagggttag ggttagggtt agggttaggg ttagggttag ggttagggtt agggttaggg      120
ttagggttag ggttagggtt agggttaggg ttagggttag ggttagggtt agggttaggg      180

<210> SEQ ID NO 75
<211> LENGTH: 545
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
caccgagatt ctcccaaggc aaggcgaggg gctgcattgc agggtccagt tgcagcgttg      60
aaacacaaat gcagcattcc taatgcaccc atgacagcta aaatataaca cccacattgc      120
tcatgtggtt agggtgaggg tgaggtcgg ttagggttgg ggttagggtt agggttaggg      180
ttagggttag ggtaagggtt aagggttaag ggttaaggtt ggggttgggg ttggggttgg      240
ggttggggta ggggtagggt tagggttag ggttagggta gggttagggt tagggttagg      300
gttagggtag gggttagggg ttaggggtta ggggttaggg gttagggtta gggttagggt      360
aggggttagg gttagggtta gggttagggt taggggtagg ggttagggtt agggttaggg      420
ttagggttag ggttagggtt agggttaggg ttagggttag ggttagggtt agggttaggg      480
tttgggttag ggttagggtt agggttaggg ttagggttag ggtcaggcgc agagacacat      540
gctag                                                                 545

<210> SEQ ID NO 76
<211> LENGTH: 255
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
caccgagatt ctcccaaggc aaggggaggg gctgcattgc agggtccact tgcagcgtcg      60
gaacgcaaat gcagcattcc taatgcacac atgatacca aaatataaca cccacattcc      120
tcatgtgctt acggtgaggg tgaggtgag ggtgggggtg ggggtggggg ttggggttgg      180
ggttagggtt cgggttcggg ttcgggttcg gagagaggcg cgccgcgccg gcgcaggcgc      240
agagacacat gctag                                                      255

<210> SEQ ID NO 77

<211> LENGTH: 868
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

| | | | | | |
|---|---|---|---|---|---|
| caccgagatt | ctcccaaggc | aaggcgaggg | gctgtattgc | agggttcaac | tgcagcgtcg | 60 |
| caactcaaat | gcagcattcc | taatgcacac | atgacaccca | aaatataaca | gacatattac | 120 |
| tcatggaggg | ttagggttgg | ggttgggtt | ggggttgggg | ttagggttag | ggttagggtt | 180 |
| aggggttagg | gttaggggtt | agggttaggg | ttaaggtta | gggttaaggg | ttagggttag | 240 |
| ggttagggtt | agggttaggg | ttagggttta | gggtttagcg | gttagggttg | gggttggcgt | 300 |
| tggggtaggg | gttgggggttg | gggtaggggt | aggggtggg | gttggggtag | gggtagggt | 360 |
| agggttaggg | ttagggttag | ggttaggggt | tagggttagg | gatagacatg | aagatggggt | 420 |
| cacctcccat | ccaccagcaa | cctccctgta | cactgccgca | ggtgcagcag | cagttctttg | 480 |
| cactgggagc | caatgagagt | gtgcactggg | ggaaagcatt | tttcacactt | ttcatgtctg | 540 |
| ttgccctcta | cccccaagt | aaaccctgac | ttctggggct | ttcacagtgg | taaagtgagc | 600 |
| acaattacag | aatctaccta | atagggctgt | ctgtatgtca | atggacttgg | cctgtgcctg | 660 |
| aggaaatgct | agccccatga | tcctgcagcc | atggttagga | aggacacggc | agggaatggg | 720 |
| acctttcaca | gaccgggccg | tggccagcag | ccagggccga | ctcaccgaga | caatggcga | 780 |
| gcatctgagt | ggctttcctt | tggtcatagg | cgtggcgcag | gcgcagagag | gcgcgccgtg | 840 |
| ctgccgcagg | cgcagagaca | catgctag | | | | 868 |

<210> SEQ ID NO 78
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

| | | | | | |
|---|---|---|---|---|---|
| caccgagatt | ctcccaaggc | aaggcgaggg | gctgtattgc | agggttcaag | tgcagcgtca | 60 |
| gaactcaaat | gcagcattcc | taatgcacac | atgacaccct | aaatataaca | ggcatattac | 120 |
| tcatggaggg | ttagggttca | cgttcgggct | cgggttcggg | ttcgggttcg | ggttcgggtt | 180 |
| aggggggttag | ggttagggtt | ggggttgggg | tcggggtcgg | ggtcgggtc | agggttaggg | 240 |
| ttagggtagg | gtcggggtcg | gggtcggcag | gcgcagagac | acatgctagc | gcgtccaggg | 300 |
| gaggaggcgt | ggcacaggcg | cagagacaca | tgctag | | | 336 |

<210> SEQ ID NO 79
<211> LENGTH: 346
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

| | | | | | |
|---|---|---|---|---|---|
| caccgagatt | ctcccaaggc | aaggcgaggg | gctgtattgc | agggttaggg | ttagggttag | 60 |
| ggttacggtt | agggttaggg | ttagggttag | ggttagggtt | agggttaggg | cagggttagg | 120 |
| gttagggtta | gggttagggg | ttagggttac | ggttagggtt | aggggttagg | gttagggtga | 180 |

```
gggtgagggt gagggtgagg gttagggtga gggtgagggt gagggtgagg gttagggtta    240
gggttaggca ggcgcagaga ggcgcgccgc gccggcgcag gcgcagagac acatgctagc    300
gcgtccaggg gaggaggcgt ggcacaggcg cagagacaca tgctag                   346

<210> SEQ ID NO 80
<211> LENGTH: 307
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
caccgagatt ctcccaaggc aaggcgaggg gctgcattgc agggtccagt tgcagcgttg     60
gaatacaaat gcagcattcc taatgcacac atgacaccta aaatataaca cccacattgc    120
tcatgtggtg agggtgaggg tgagggcgag gggttgggtt ggggttgggg ttggggttgg    180
gattggggtt agtgttaggg ttaagggtta ggtttagggt tagggtaggg ttggggttgg    240 gttgggggttg gggttgggggt tagggttagg gttaagggtt agggtcaggc gcagagacac    300
atgctag                                                              307

<210> SEQ ID NO 81
<211> LENGTH: 209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
caaggcaagg cgaggggctg cattgcaggg tccagttgca gcgttggaat acaaatgcag     60
cattcctaat gcacacatga cacctaaaat ataacaccca cattgctcat gtggtgaggg    120
tgagggtgag ggtgaggggt tgggttgggg ttggggttgg ggcgcagaga ggcgcgccgc    180
gccggcgcag gcgcagagac acatgctag                                      209

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ttagggttag ggttagggtt agggttaggg ttaggg                               36
```